United States Patent [19]

Ashikari et al.

[11] Patent Number: 5,084,385
[45] Date of Patent: * Jan. 28, 1992

[54] PROCESS FOR PRODUCING ALCOHOL USING YEAST TRANSFORMED BY RHIZOPUS GLUCOAMYLASE GENE

[75] Inventors: Toshihiko Ashikari; Norihisa Nakamura; Yoshikazu Tanaka; Yuji Shibano; Hajime Yoshizumi, all of Osaka, Japan

[73] Assignee: Suntory Limited, Osaka, Japan

[*] Notice: The portion of the term of this patent subsequent to Sep. 5, 2006 has been disclaimed.

[21] Appl. No.: 338,395

[22] Filed: Apr. 14, 1989

Related U.S. Application Data

[63] Continuation of Ser. No. 808,743, Dec. 13, 1985, abandoned.

[30] Foreign Application Priority Data

Dec. 15, 1984 [JP] Japan .................. 59-264965

[51] Int. Cl.$^5$ .................. C12P 7/06; C12P 7/14; C12N 9/34; C12N 15/52
[52] U.S. Cl. .................. 435/96; 435/161; 435/162; 435/172.3; 435/205; 435/939; 935/10; 935/28
[58] Field of Search ............ 435/162, 161, 172.3, 435/205, 939, 96; 935/10, 28

[56] References Cited

U.S. PATENT DOCUMENTS 4,514,496 4/1985 Yoshizumi et al. ............... 435/162

FOREIGN PATENT DOCUMENTS 0073635 3/1983 European Pat. Off. .
0109559 5/1984 European Pat. Off. .
0109560 5/1984 European Pat. Off. .
0126206 11/1984 European Pat. Off. .
0163491 12/1985 European Pat. Off. .
0186066 7/1986 European Pat. Off. .
2089836 6/1982 United Kingdom .

OTHER PUBLICATIONS

"Synthetic DNA and medicine"—, —Riggs and Itakura in Am. J. Hum. Genet. 31, 531–538, 1979.
"Isolation of two inactive fragments of a Rhizopus sp. Glucoamylase relationship among three forms of the enzyme and the isolated fragments"—Takahashi, Tsuchida and Irie in J. Biochem., vol. 92, No. 5, 1982, pp. 1623–1633.
Chemical abstract—vol. 97, 67146y, p. 150—Aug. 1982.
Food Technology, vol. 38 (Feb. 1984) No. 2, "Genetic manipulation of Brewing and Related Yeast Strains", Panchal, Russell, Sills and Stewart—pp. 99–106 & 111.
"Genetic Development of yeast strains"—Tubb, Sep. 1984 in Brewers Guardian, pp. 34–37.

Primary Examiner—Jacqueline Stone
Assistant Examiner—Keith D. Hendricks
Attorney, Agent, or Firm—Cushman, Darby & Cushman

[57] ABSTRACT

This invention provides a process for producing ethanol from a starchy material, wherein the starchy material is simultaneously subjected to saccharification and subsequent fermentation by use of a yeast host which has been transformed by an expressible recombinant vector comprising a glucoamylase gene derived from a fungus of the genus Rhizopus.

6 Claims, 19 Drawing Sheets

Fig. 1(a)

```
GATCTCAATT TGTGTTGTGA TATATTCAGA TTTAAAATTT CAAACATATA TAAGACGCGT TTATTCCTC GTTTTCAAA AATCATCACT
                                                     60
TGTCTTCAAA TTGATCTTTC TCTA ATG CAA CTG TTC AAT TTG CCA TTG AAA GTT TCA TTC TTT CTC GTC CTC TCT TAC
                         120
              MET GLN LEU PHE ASN LEU PRO LEU LYS VAL SER PHE PHE LEU VAL LEU SER TYR
                                                                                        240
TTT TCT TTG CTC GTT TCT GCT GCA AGC ATT CCT AGT AGT GCT TCT GTC CAG CTT GAT TCA TAC AAT TAC GAT
PHE SER LEU VAL SER ALA Ala Ser Ile Pro Ser Ser Ala Ser Val Gln Leu Asp Ser Tyr Asn Tyr Asp
 180                                                                  300
GGC TCT ACT TTT TCA GGA AAA ATT TAT GTC AAG AAC ATT GCT TAC TCC AAG AAG GTT ACT GTA ATT TAC GCC
Gly Ser Thr Phe Ser Gly Lys Ile Tyr Val Lys Asn Ile Ala Tyr Ser Lys Lys Val Thr Val Ile Tyr Ala
GAT GGC TCT GAC AAC TGG AAT AAT AAT GGA AAC ACC ATT GCT GCT TCT TAC TCT GCT CCT ATT TCT GGA TCA
Asn Gly Ser Asp Asn Trp Asn Asn Asn Gly Asn Thr Ile Ala Ala Ser Tyr Ser Ala Pro Ile Ser Gly Ser
                                                360
                                                                          420
AAT TAC GAA TAC TGG TGG ACA TTC TCT GCC TCC ATT AAT GGT ATC AAG GAG TTC TAC ATT AAG TAT GAG GTC AGT
Asn Tyr Glu Tyr Trp Trp Thr Phe Ser Ala Ser Ile Asn Gly Ile Lys Glu Phe Tyr Ile Lys Tyr Glu Val Ser
GGA AAA ACA TAC TAT TAT GAT AAC AAC AAT TCT GCC AAT AGC GCC AAT TAC CAA GTA TCT ACA TCC AAG CCT ACT ACT ACT
Gly Lys Thr Tyr Tyr Tyr Asp Asn Asn Asn Ser Ala Asn Ser Ala Asn Tyr Gln Val Ser Thr Ser Lys Pro Thr Thr Thr Thr
         480
                                                                                              600
GCT ACT GCT ACT ACT ACC GCT CCT CCT ACT TCA ACC ACT ACG ACT TCA ACC CCC TCA AGC TCT GAG CCA GCT ACT
Ala Thr Ala Thr Thr Thr Ala Pro Pro Thr Ser Thr Thr Thr Thr Ser Thr Pro Pro Ser Ser Glu Pro Ala Thr
        540                                                         660
TTC CCA ACT GGT AAC TCT ACA ATC TCC TCA TGG ATT AAG AAG CAA GAA GGT ATC AGC TTT GCT ATG CTT
Phe Pro Thr Gly Asn Ser Thr Ile Ser Ser Trp Ile Lys Lys Gln Glu Gly Ile Ser Arg Phe Ala Met Leu
```

Fig. 1(b)

```
CGA AAC ATC AAT CCT GGA AGC GCT ACC GGT TTC ATT GCT GCC TCA CTC TCT ACC GCT GGT CCC GAT TAC
Arg Asn Ile Asn Pro Gly Ser Ala Thr Gly Phe Ile Ala Ala Ser Leu Ser Thr Ala Gly Pro Asp Tyr
                                                    720

TAC TAT GCT TGG ACT CGT GAT GCT GCA TTA ACC TCC AAT GTA ATT GTT TAC GAA TAC AAC ACT ACT TTG TCC
Tyr Tyr Ala Trp Thr Arg Asp Ala Ala Leu Thr Ser Asn Val Ile Val Tyr Glu Tyr Asn Thr Thr Leu Ser
                                780

GGT AAT AAG ACT ATC CTC AAC GTC CTC AAG GAC TAT GTT ACA TTC TCA GTC AAG ACC CAA TCA ACT TCT ACC
Gly Asn Lys Thr Ile Leu Asn Val Leu Lys Asp Tyr Val Thr Phe Ser Val Lys Thr Gln Ser Thr Ser Thr
            840                                                                              960

GTC TGT AAC TGC CTT GGT GAG CCT AAG TTC AAT CCT GAT GGT TCT GGC TAT ACT GGT GCT TGG GGA AGA CCT
Val Cys Asn Cys Leu Gly Glu Pro Lys Phe Asn Pro Asp Gly Ser Gly Tyr Thr Gly Ala Trp Gly Arg Pro
        900

CAA AAT GAT GGA CCT GCT GAA CGT GCT ACT CTC AAG CCT GCT ACC TTT GCT GAC AGT TAT CTT ACT CAA ACA AAG
Gln Asn Asp Gly Pro Ala Glu Arg Ala Thr Leu Lys Pro Ala Thr Phe Ala Asp Ser Tyr Leu Thr Gln Thr Lys
                                                                1020

GAT GCT TCC TAT GTC ACT GGT ACA CTC ACT GGT TTA TGG GAA GAA TTC ATC TTC AAG GAC TTG GAC TAT GTC GTC AAT GTC TGG
Asp Ala Ser Tyr Val Thr Gly Thr Leu Thr Gly Leu Trp Glu Glu Phe Ile Phe Lys Asp Leu Asp Tyr Val Val Asn Val Trp
                                                        1080

TCT AAT GGC TGT TTC TTC GAT TTA TGG GAA GAA GAT TTC GCT GAC GGT GTT CAC TTC TAT ACT TTA ATG GTT ATG CGT AAG
Ser Asn Gly Cys Phe Phe Asp Leu Trp Glu Glu Asp Phe Ala Asp Gly Val His Phe Tyr Thr Leu Met Val Met Arg Lys

GGT TTG CTT CTT GGT GCA GAT TTC GCT AAA CGT AAC GGT GAC TCT ACT CGT GCA TCT ACC TAT AGC AGC ACT
Gly Leu Leu Leu Gly Ala Asp Phe Ala Lys Arg Asn Gly Asp Ser Thr Arg Ala Ser Thr Tyr Ser Ser Thr
                            1200                                                            1320

GCA TCC ACT ATT GCA AAC AAG ATC TCT AGC TTC TGG GTT TCT AAT AAC TGG ATT CAA GTC AGT CAA AGC
Ala Ser Thr Ile Ala Asn Lys Ile Ser Ser Phe Trp Val Ser Asn Asn Trp Ile Gln Val Ser Gln Ser
        1260
```

Fig.1(c)

```
                                                          1380
GTT ACT GGT GGT GTC AGT AAA AAG GGT TTG GAT GTC TCC ACA TTG GCT GCT AAC CTT GGT AGT GTT GAT
Val Thr Gly Gly Val Ser Lys Lys Gly Leu Asp Val Ser Thr Leu Ala Ala Asn Leu Gly Ser Val Asp

1440
GAT GGA TTC TTC ACT CCT GGC TCT GAA AAG ATC CTT GCC ACT GCT GTT GAA GAC TCC TTC GCT TCC
Asp Gly Phe Phe Thr Pro Gly Ser Glu Lys Ile Leu Ala Thr Ala Val Glu Asp Ser Phe Ala Ser

1500
TTG TAT CCT ATC AAC AAA CTT CCA TCT TAC CTT GGT AAC TCT ATT GGT AGA TAT CCT GAA GAC ACT TAC
Leu Tyr Pro Ile Asn Lys Leu Pro Ser Tyr Leu Gly Asn Ser Ile Gly Arg Tyr Pro Glu Asp Thr Tyr

1560
AAT GGT AAC GGA AAC TCT CAA GGA AAC TCT TGG TTC TTG GCT GTA ACT GGT TAC GCT GAG CTC TAT TAC CGT
Asn Gly Asn Gly Asn Ser Gln Gly Asn Ser Trp Phe Leu Ala Val Thr Gly Tyr Ala Glu Leu Tyr Tyr Arg

1680
GCC ATC AAG GAA TGG ATC GGC AAC GGT GTC ACT GTC AGC AGT ATA AGT TTA CCC TTC TTC AAG AAG TTT
Ala Ile Lys Glu Trp Ile Gly Asn Gly Val Thr Val Ser Ser Ile Ser Leu Pro Phe Phe Lys Lys Phe

1740
GAT TCA TCT GCT ACA ACT GGA AAG AAG TAC ACT GTT GGT ACT TCC GAC TTT AAC AAC AAT GGA TCT CTT GCT CAA AAT ATT
Asp Ser Ser Ala Thr Thr Gly Lys Lys Tyr Thr Val Gly Thr Ser Asp Phe Asn Asn Asn Gly Ser Leu Ala Gln Asn Ile

1800
GCA CTC GCT GCT GCT GAC CGT TTC TTG TCC ACT GTC CAG CTC CAT GCT CAC AAC AAT AAC TGG TCT CTT GCT GAA GAG
Ala Leu Ala Ala Ala Asp Arg Phe Leu Ser Thr Val Gln Leu His Ala His Asn Asn Asn Trp Ser Leu Ala Glu Glu

1860
TTT GAC CGC ACC ACT ACT GGT TTA TCC ACC GGT GCT AGA GAC TTG ACC TGG TCT CAC GCT TCT TTA ATC ACC GCT
Phe Asp Arg Thr Thr Thr Gly Leu Ser Thr Gly Ala Arg Asp Leu Thr Trp Ser His Ala Ser Leu Ile Thr Ala

1920
TCT TAC GCT AAG GCT GGT GCA CCT GCC GCT TAAGCTGTAA ATTTAAATGC AAAGCATTAC AGCTTATTTT CTTTTTCAAA
Ser Tyr Ala Lys Ala Gly Ala Pro Ala Ala

TAAAAACATA TTGATATGTT CATAACAAAA AAAAAAAAAA
```

Fig. 2(a)

```
         10         20         30         40         50         60         70         80         90
GATCTCAATT TGTGTTGTGA TATATTCAGA TTTAAAATTT CAAACATATA TAAGACGCGT TTATTCCTC GTTTTCAAA AATCATCACT
        100        110
TGTCTTCAAA TTGATCTTTC TCTA ATG CAA CTG TTC AAT TTG CCA TTG AAA GTT TCA TTC TTT CTC GTC CTC TCT TAG
                         MET GLN LEU PHE ASN LEU PRO LEU LYS VAL SER PHE PHE LEU VAL LEU SER TYR
                     150                                                                      240
    180                                       210
TTT TCT TTG CTC GTT TCT TCT GCA AGC ATT CCT AGT AGT GCT TCT GTC CAG CTT GAT TCA TAC AAT TAC GAT
PHE SER LEU LEU VAL SER ALA ALA SER ILE PRO SER SER ALA SER VAL GLN LEU ASP SER TYR ASN TYR ASP
                                                                                         317
GGC TCT ACT TTT TCA GGA AAA ATT TAT gtaggttgca tataattcaa acattaaaaa aatattaatg ttcatgctgt acgctgt
Gly Ser Thr Phe Ser Gly Lys Ile Tyr                                  INTRON
   341                                     371
ag GTC AAG AAC ATT GCT TAC TCC AAG AAG GTT ACT GTA ATT TAC GCC GAT GGC TCT GAC AAC TGG AAT AAT AAT
   Val Lys Asn Ile Ala Tyr Ser Lys Lys Val Thr Val Ile Tyr Ala Asn Gly Ser Asp Asn Trp Asn Asn Asn
401                                                          461
GGA AAC ACC ATT GCT TCT TAC TCT GCT CCT ATT TCT GGA TCA AAT TAC GAA TAC TGG ACA TTC TCT GCC
Gly Asn Thr Ile Ala Ala Ser Tyr Ser Ala Pro Ile Ser Gly Ser Asn Tyr Glu Tyr Trp Thr Phe Ser Ala
      491                                        523                                       543
TCC ATT AAT GGT ATC AAG GAG TTC TAC ATT AAG gtaacttatt tttactttat gatatttgcc cttatactta attaactaac
Ser Ile Asn Gly Ile Lys Glu Phe Tyr Ile Lys                                  INTRON
      563                                        581                                            611
ccttttctct ctatag TAT GAG GTC AGT GGA AAA ACA TAC TAT GAT AAC AAC AAT TCT GCC AAT TAC CAA Ggt aaag
                  Tyr Glu Val Ser Gly Lys Thr Tyr Tyr Asp Asn Asn Asn Ser Ala Asn Tyr Gln Val
       636                                        656                                       680                   710
ataata atatacaaat gcctacaact attcacattt ttatagTA TCT ACA TCC AAG CCT ACA TCC ACT GCT ACT
                                  INTRON          Ser Thr Ser Lys Pro Thr Thr Thr Thr Ala Thr Ala
```

Fig.2(b)

```
ACT ACT ACC GCT CCT TCC ACT TCA ACG ACT CCC CCC TCA AGC TCT GAG CCA GCT ACT TTC CCA ACT
Thr Thr Thr Ala Pro Ser Thr Ser Thr Thr Pro Pro Ser Ser Ser Glu Pro Ala Thr Phe Pro Thr
                            740                            770

GGT AAC TCT ACA ATC TCC TCA TGG ATT AAG AAG CAA GAA GGT ATC AGC CGC TTT GCT ATG CTT CGA AAC ATC
Gly Asn Ser Thr Ile Ser Ser Trp Ile Lys Lys Gln Glu Gly Ile Ser Arg Phe Ala Met Leu Arg Asn Ile
            800                            830

AAT CCT GGA AGC GCT ACC GGT TTC ATT GCC TCA CTC TCT ACC GAT TAC CCC GAT TAC TAC TAT GCT
Asn Pro Gly Ser Ala Thr Gly Phe Ile Ala Ala Ser Leu Ser Thr Ala Gly Pro Asp Tyr Tyr Tyr Ala
    860                            890                            920

TGG ACT CGT GAT GCT GCA TTA ACC TCC AAT GTA ATT TAC GAA TAC GTC AAG ACC CAA ACT TCT GGT AAT AAG
Trp Thr Arg Asp Ala Ala Leu Thr Ser Asn Val Ile Tyr Glu Tyr Val Lys Thr Gln Thr Ser Gly Asn Lys
                950                            980                           1070

ACT ATC CTC AAC GTC CTC CTC AAG GAC TAT GTT ACA TTC TCA GTC TAT ACT GGT TCT GAT GGT TCC ACC GTC TGT AAC
Thr Ile Leu Asn Val Leu Leu Lys Asp Tyr Val Thr Phe Ser Val Tyr Thr Gly Ser Asp Gly Leu Thr Val Cys Asn
                            1010                          1040

TGC CTT GGT GAG CCT AAG CCT AAT CCT GAT GGT TCT GGC TAT ACT GGT TAT GAC AGT TAT CTT ACT CAA ACA AAG GAT GCT TCC
Cys Leu Gly Glu Pro Lys Pro Asn Pro Asp Gly Ser Gly Tyr Thr Gly Tyr Asp Ser Tyr Leu Thr Gln Thr Lys Asp Ala Ser
                        1100                           1130

GGA CCT GCT GAA CGT GCT GCT ACT TTG TTT GCT GAC TTG TTT ACT ATT CTT ACT GTC AAT GTC GTC AAT GAT
Gly Pro Ala Glu Arg Ala Ala Thr Leu Phe Ala Asp Leu Phe Leu Thr Ile Leu Thr Val Asn Val Val Asn Gly
        1160                          1190                          1250                         1280

TAT GTC ACT GGT ACA CTC AAG CCT ATC TTC AAG GAC TAT GTC AAT GTC GTC AAT TGG TCT AAT GGC
Tyr Val Thr Gly Thr Leu Thr Lys Pro Ile Phe Lys Asp Tyr Val Leu Asp Tyr Val Asn Val Trp Ser Asn Gly
                    1220

TGT TTC GAT TTA TGG GAA GAA GTC AAC GGT GTT CAC TTC TAT ACT TTA ATG GTT ATG CGT AAG GGT TTG CTT
Cys Phe Asp Leu Trp Glu Glu Val Asn Gly Val His Phe Tyr Thr Leu Met Val Met Arg Lys Gly Leu Leu
                                            1310                               1340
```

Fig.2(c)

```
                                                               1400                                                           1430
CTT GGT GCA GAT TTC GCT AAA CGT AAC GGT GAC TCT GAC TCT ACT CGT GCA TCT ACC TAT AGC AGC ACT GCA TCC ACT
Leu Gly Ala Asp Phe Ala Lys Arg Asn Gly Asp Ser Asp Ser Thr Arg Ala Ser Thr Tyr Ser Ser Thr Ala Ser Thr

1490
ATT GCA AAC AAG ATC TCT AGC TTC TGG GTT TCT TCT AAT AAC TGG ATT CAA GTC AGT CAA AGC GTT ACT GGT
Ile Ala Asn Lys Ile Ser Ser Phe Trp Val Ser Ser Asn Asn Trp Ile Gln Val Ser Gln Ser Val Thr Gly 1520                                                       1550
GGT GTC AGT AAA AAG GGT TTG GAT GTC TCC ACA TTG TTG GCT AAC CTT GGT AGT GTT GAT GAT GGA TTC
Gly Val Ser Lys Lys Gly Leu Asp Val Ser Thr Leu Leu Ala Asn Leu Gly Ser Val Asp Asp Gly Phe 1580                                                  1605                                                 1625                                                    1645
TTC ACT CCT GGC TCT GAA AAG gtaaattaac atgcataaaa gaataagact ataacattac taattcacat tttctactca g
Phe Thr Pro Gly Ser Glu Lys                                  INTRON 1680                                                           1710
ATC CTT GCC ACT GCT GTT GAA GAC TCC TTT GCT TCC TTG TAT CCT ATC AAC AAA AAC CTT CCA TCT
Ile Leu Ala Thr Ala Val Glu Asp Ser Phe Ala Ser Leu Tyr Pro Ile Asn Lys Asn Leu Pro Ser 1770                                                                1800
TAC CTT GGT AAC TCT ATT GGT AGA TAT CCT GAA GAC ACT TAC AAT GGT TAC CGT GCC ATC AAG GAA TGG ATC GGC AAC GGT TCT
Tyr Leu Gly Asn Ser Ile Gly Arg Tyr Pro Glu Asp Thr Tyr Asn Gly Tyr Arg Ala Ile Lys Glu Trp Ile Gly Asn Gly Ser 1740                                                                 1830                                                       1860
TGG TTC TTG GCT GTA ACT GGT TAC GCT GAG CTC TAT TAC CGT GCC ATC AAG GAA TGG ATC GGC AAC GGT GGT
Trp Phe Leu Ala Val Thr Gly Tyr Ala Glu Leu Tyr Tyr Arg Ala Ile Lys Glu Trp Ile Gly Asn Gly Gly 1890                                                                  1920
GTC ACT GTC AGC AGC ATA AGT TTA CCC TTC TTC AAG AAG TTT GAT TCA TCT GCT ACA TCT GCT ACA TCT GGA AAG AAG TAC
Val Thr Val Ser Ser Ile Ser Leu Pro Phe Phe Lys Lys Phe Asp Ser Ser Ala Thr Ser Ala Thr Ser Gly Lys Lys Tyr 1950                                                     1980                                                                   2010
ACT GTT GGT ACC TCC GAC TTT AAC AAC CTT GCT CAA AAT ATT GCA CTC GCT GCT GAC CGT GTT TTC TCC ACT
Thr Val Gly Thr Ser Asp Phe Asn Asn Leu Ala Gln Asn Ile Ala Leu Ala Ala Asp Arg Val Phe Ser Thr
```

Fig. 2(d)

```
                                    2040                                             2070
GTC CAG CTC CAT GCT CAC AAC AAT GGA TCT CTT GCT GAA GAG TTT GAC CGC ACC ACT GGT TTA TCC ACC GGT
Val Gln Leu His Ala His Asn Asn Gly Ser Leu Ala Glu Glu Phe Asp Arg Thr Thr Gly Leu Ser Thr Gly
                2100                                    2130                                            2160
GCT AGA GAC TTG ACC TGG TCT CAC GCT TCT TTA ATC ACC GCT TCT TAC GCT AAG GCT GGT GCA CCT GCC GCT
Ala Arg Asp Leu Thr Trp Ser His Ala Ser Leu Ile Thr Ala Ser Tyr Ala Lys Ala Gly Ala Pro Ala Ala
                            2190                                        2230
TAAGCTGTAA ATTTAAATGC AAAGCATTAC AGCTTATTTT CTTTTTCAAA TAAAAACATA TTGATATGTT CATAACATTT TCTTGTT
                2270
TGT TGTACTGTAA TATGGGTAAC CACATAAGCA TAAACAGCAA
```

Fig. 3(a)

```
                                          50
     AAATT TATGTCAAGA ACATTGCTTA CTCCAAGAAG GTTACTGTAA TTTACGCCGA TGGCTCTGAC AACTGGAATA
100                                      150
ATAATGGAAA CACCATTGCT GCTTCTTACT CTGCTCCTAT TTCTGGATCA AATTACGAAT ACTGGACATT CTCTGCCTCC ATTAATGGTA
         200                                      250
TCAAGGAGTT CTACATTAAG TATGAGGTCA GTGGAAAAAC ATACTATGAT AACAACAATT CTGCCAATTA CCAAGTATCT ACATCCAAGC
                                 300                                      350
CTACTACTAC TACTGCTACT GCTACTACTA CTACCGCTCC TTCCACTTCA ACCACGACTC CCCCCTCAAG CTCTGAGCCA GCTACTTTCC
                         400                                      450
CAACTGGTAA CTCTACAATC TCCTCATGGA TTAAGAAGCA AGAAGGTATC AGCCGCTTTG CTATGCTTCG AAACATCAAT CCTCCTGAA
                 500                                      550
GCGCTACCGG TTTCATTGCT GCCTCACTCT CTACCGCTGG TCCCGATTAC TACTATGCTT GGACTCGTGA TGCTGCATTA ACCTCCAATG
         550                                      600
TAATTGTTTA CGAATACAAC ACTACTTTGT CCGGTAATAA GACTATCCTC AACGTCCTCA AGGACTATGT TACATTCTCA GTCAAGACCC
 650                                      700
AATCAACTTC TACCGTCTGT AACTGCCTTG GTGAGCCTAA GTTCAATCCT GATGGTTCTG GCTATACTGG TGCTTGGGGA AGACCTCAAA
                                 750                                      800
ATGATGGACC TGCTGAACGT GCTACTACCT TCATTTTGTT TGCTGACAGT TATCTTACTC AAACAAAGGA TGCTTCCTAT GTCACTGGTA
                         850                                      900
CACTCAAGCC TGCTATCTTC AAGGACTTGG ACTATGTCGT CAATGTCTGG TCTAATGGCT GTTTCGATTT ATGGGAAGAA GTCAACGGTG
```

Fig. 3(b).

```
                                                      950
TTCACTTCTA TACTTTAATG GTTATGCGTA AGGGTTTGCT TCTTGGTGCA GATTTCGCTA AACGTAACGG TGACTCTACT CGTGCATCTA
       1000                                                  1050
CCTATAGCAG CACTGCATCC ACTATTGCAA ACAAGATCTC TAGCTTCTGG GTTTCTTCTA ATAACTGGAT TCAAGTCAGT CAAAGCGTTA
                   1100                                                 1150
CTGGTGGTGT CAGTAAAAAG GGTTTGGATG TCTCCACATT GTTGGCTGCT AACCTTGGTA GTGTTGATGA TGGATTCTTC ACTCCTGGCT
                              1200                                                 1250
CTGAAAAGAT CCTTGCCACT GCTGTTGCTG TTGAAGACTC CTTCGCTTCC TTGTATCCTA TCAACAAAAA CCTTCCATCT TACCTTGGTA
                                         1300                                                 1350
ACTCTATTGG TAGATATCCT GAAGACACTT ACAATGGTAA CGGAAACTCT CAAGGAAACT CTTGGTTCTT GGCTGTAACT GGTTACGCTG
                                                    1400
AGCTCTATTA CCGTGCCATC AAGGAATGGA TCGGCAACGG TGGTGTCACT GTCAGCAGCA TAAGTTTACC CTTCTTCAAG AAGTTTGATT
       1450                                                  1500
CATCTGCTAC ATCTGGAAAG AAGTACACTG TTGGTACCTC CGACTTTGCTC AACCTTGCTC AAAATATTGC ACTCGCTGCT GACCGTTTCT
                   1550                                                 1600
TGTCCACTGT CCAGCTCCAT GCTCACAACA ATGGATCTCT TGCTGAAGAG TTTGACCGCA CCACTGGTTT ATCCACCGGT GCTAGAGACT
                              1650                                                 1700
TGACCTGGTC TCACGCTTCT TTAATCACCG CTTCTTACGC TAAGGCTGGT GCACCTGCCG CTTAAGCTGT AAATTTAAAT GCAAAGCATT
                                         1750
ACAGCTTATT TTCTTTTTCA AATAAAAACA TATTGATATG TTCATAACAA AAAAAAAAAA
```

5,084,385

PROCESS FOR PRODUCING ALCOHOL USING YEAST TRANSFORMED BY RHIZOPUS GLUCOAMYLASE GENE

This is a continuation of application Ser. No. 06/808,743, filed Dec. 13, 1985, now abandoned.

FIELD OF THE INVENTION

The present invention relates to a process for producing a glucoamylase and alcohol using a yeast which is engineered by recombinant DNA technology so as to acquire the ability to produce glucoamylase derived from *Rhizopus oryzae*.

PRIOR ART

Glucoamylase is an enzyme which hydrolyzes starch into glucose from the non-reducing terminal and, therefor is widely used for saccharifying starch in the production of ethanol from starchy materials The glucoamylase derived from the genus Rhizopus is produced in particularly high productivity and high enzyme activity. Furthermore, in contrast to common glucoamylase, Rhizopus glucoamylase exhibits a strong action on raw starch and its enzymological and chemical properties including optimum pH are particularly suitable for the saccharification of cereal starch. Because of these features, the Rhizopus-derived glucoamylase is considered to be best suited to alcohol production by non-cooking or low-temperature cooking techniques (see U.S. Pat. Nos. 4,514,496 and 4,092,434).

However, Rhizopus glucoamylase is usually produced by cultivation on a solid medium using wheat bran as the principal substrate, and this increases the cost of enzyme production as compared with a liquid culture which can be carried out on a tank scale, and hence alcohol production using glucoamylase will be expensive.

SUMMARY OF THE INVENTION

The present inventors assumed that the above problem could be resolved if the glucoamylase gene of Rhizopus was incorporated into a host yeast so that it can be expressed. Such yeast can directly utilize starch including low temperature cooked starchy materials and non-cooked starchy materials, thereby reducing the cost of ethanol production in the process of producing said alcohol from starch by saving or even avoiding the use of Rhizopus glucoamylase preparation for saccharifying starch. The inventors conducted extensive research on the basis of the above assumption in order to complete the present invention.

BRIEF DESCRIPTION OF THE DRAWINGS

FIGS. 1a–c show the nucleotide sequence of the intron-free glucoamylase structural gene of the invention together with the signal peptide region;

FIGS. 2a–d show the nucleotide sequence of a glucoamylase gene cloned from the chromosomal DNA or *Rhizopus oryzae*;

FIG. 3a–b show the nucleotide sequence of the C-terminal region of a glucoamylase gene cloned from the cDNA obtained from the mRNA of *Rhizopus oryzae*;

FIGS. 5, 6A, 6B and 6C are flowsheets showing the steps for constructing, in a plasmid vector, an intron-free cDNA of the complete length by combining the two genes shown in FIG. 4, and for incorporating a promoter and a tail with a view to ensuring efficient gene expression in yeast, wherein FIG. 5 shows the steps for producing pCGA469, FIG. 6A illustrates the steps for producing pYGA2149 and pYGA2169, and FIG. 6B depicts the steps for producing pYGIFLm222;

DETAILED DESCRIPTION OF THE INVENTION

Figure 4:
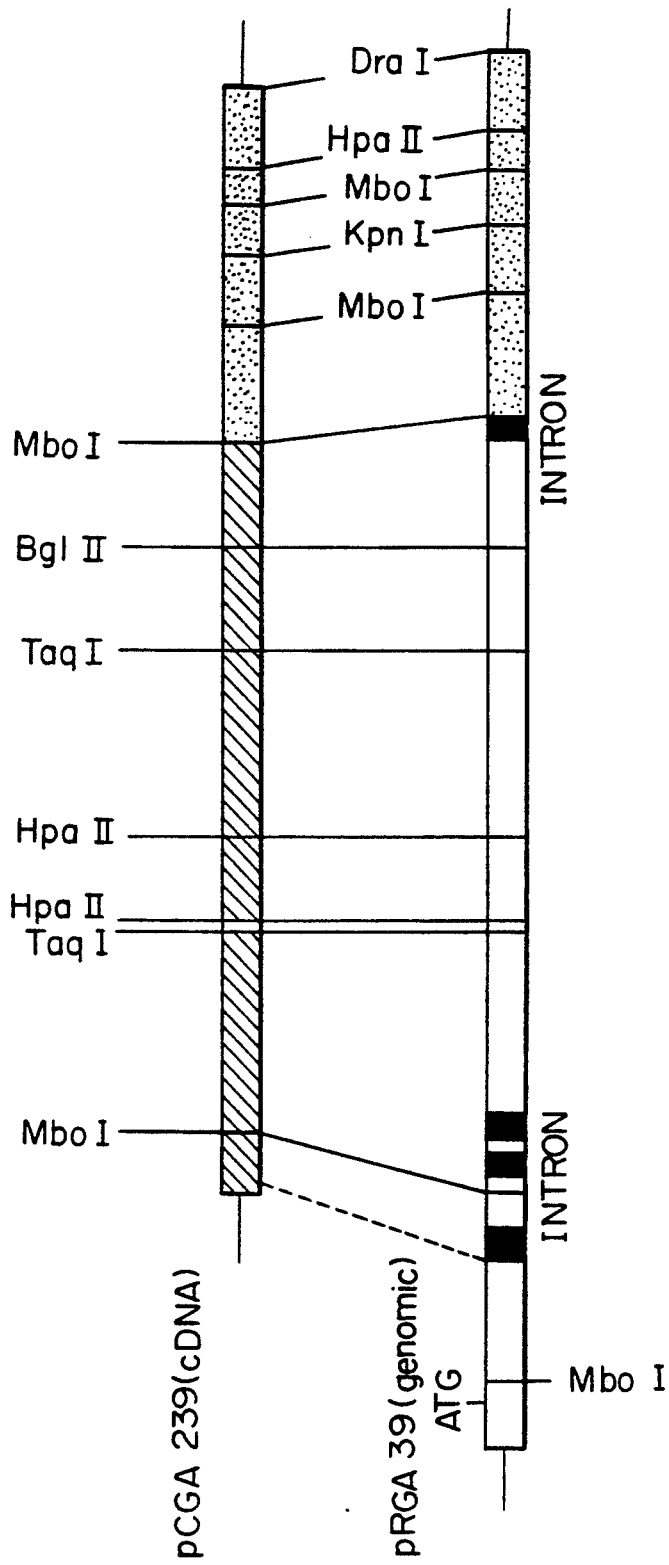
FIG. 4 compares the glucoamylase gene cloned from the chromosomal DNA of *Rhizopus oryzae* with the glucoamylase gene prepared from the mRNA of *Rhizopus oryzae*.

The present invention relates to a process for producing ethanol, wherein a glucoamylase gene derived from a filamentous fungus of the genus Rhizopus is incorporated into a recombinant vector in a manner capable of being expressed, which is then used to transform a yeast host for saccharifying starchy material to facilitate fermentation.

The starchy materials employable in the process of the invention include, for example, cereals, subterranean starches such as cassava, sweet potato, potato, as well as pure starch.

In order to produce the Rhizopus glucoamylase by a microorganism in accordance with the method of the invention, the glucoamylase gene can be prepared by an appropriate method from a filamentous fungus of the genus Rhizopus capable of producing glucoamylase, preferably *Rhizopus oryzae*; incorporating said gene into a plasmid vector capable of replicating in a host cell together with a DNA fragment comprising an expression mechanism of information such as a promoter region and a tail region which is recognized in an expression system of the host; and the host is then transformed by said vector. If yeast is used as a host, the transformed yeast produces and secretes Rhizopus glucoamylase which saccharifies any starch including non-cooked starch and hence the yeast host will convert the resulting glucose into alcohol. Thus alcohol can be produced without the addition of an expensive saccharifying enzyme from outside. It has not previously been known that alcohol may be produced by direct action of yeast on starch without previous saccharification of the starch.

The high temperature cooking process (cooked at above 120° C.), the low temperature cooking process (cooked at 60°-85° C.), and the non-cooking process are known steps for cooking or gelatinizing the raw material before saccharification in the production of alcohol. Any of the above processes may be employed in the alcohol production of the present invention.

Instead of simultaneously producing alcohol and Rhizopus glucoamylase in a yeast host, bacterial cells of Bacillus subtilis may be used as a host if Rhizopus glucoamylase is the only desired product.

According to the present invention, a method for obtaining DNA encoding the glucoamylase and the novel information of the nucleotide sequence of said DNA are also provided.

The nucleotide sequence of the DNA fragment for the production of the glucoamylase in accordance with the process of the invention can be prepared by, for example, appropriately conjugating a part of the glucoamylase nucleotide sequence cloned from chromosomal DNA of *Rhizopus oryzae* and a part of the glucoamylase cDNA sequence prepared from mRNA of *Rhizopus oryzae* as described later in more detail. To use the glucoamylase gene thus prepared for expression in yeast, the gene is preferably combined with a promoter region and/or a tail region (3' non translational region) which are suitable for transformation of the host organism (see Unexamined Published Japanese Patent Application No. 146281/1983). For example, in order to have the glucoamylase gene expressed in a yeast, the promoter region ($P_{GAP}$) and tail region ($T_{GAP}$) of the glyceraldehyde-3-phosphate dehydrogenase gene (GAP-DH), the promoter region (Ppho5) of the acid phosphatase gene (PH05), and the promoter region ($P_{PGK}$) of the 3-phosphoglycerokinase (PGK) may be employed as shown in Examples 1 and 2. A plasmid vector comprising these promoter and/or tail regions together with the gene of the present invention, as well as a microorganism transformed by such vector are preferred embodiments of the present invention.

Any fungi of the genus Rhizopus that are capable of producing glucoamylase may be used in the present invention for obtaining the desired gene. Illustrative species include *Rhizopus oryzae, Rhizopus formosaensis, Rhizopus javanicus* and *Rhizopus thailandensis.* The present inventors have confirmed that *Rhizopus oryzae* SAM 0034 (accession numbers FERM P-7960; FERM BP-929 deposited at the Fermentation Research Institute (FRI), Agency of Industrial Science and Technology, Ministery of International Trade and Industry, Japan) produces a glucoamylase particularly suitable for hydrolyzing raw starch.

The present strain (SAM 0034) has the following mycological properties.

Colonies on Potato dextrose agar medium attain a diameter of 5-5.5 mm in one day at 28° C. and cover 90 mm petri plates of Potato dextrose agar medium in two days, the colonies are white.

Colonies become grey with age.

Stolons are hyaline or yellowish brown; rhizoids brown. Sporangiophores usually arising from rhizoids, occasionally arising directly from stolons, either single or in groups, occasionally divided, 220-1200 μm long. Sporangia are globose subglobose, dark brown, 60-150 μm in diameter; columellae globose or subglobose. Sporangiospores are globose, subglobose, or angular, striatae on the surface, 5-15×3-7 μm. Chlamydospores subglobose or cylindrical, 6-13×4-19 μm.

No zygospores were observed.

At 37° C., growth occurs.

The present strain (SAM 0034) can be accommodated in the fungus genus Rhizopus, because: (1) The sporangiospores are produced within the columellate sporangium; (2) The sporangiospores are brown; (3) the rhizoids are produced.

The mycological properties of the present strain (SAM 0034) are compared with those of known species of the genus Rhizopus, referring to Inui, T., Y. Takeda & H. Iizuka, 1965, Taxonomical Studies on genus Rhizopus (Journal of General and Applied Microbiology, Vol. 11, Supplement, 121 pp. Zycha, H., R. Siepmann & G. Linnemann, 1969, Mucorales. Eine Beschreibung aller Gattungen und Arten dieser Pilzgruppe, 335 pp., J. Cramer, Lehre. Domsch, K. H., W. Gams and T. -H. Anderson, 1980, Compendium of Soil Fungi. Vol. 1, 859 pp., Academic Press. London). The result of this comparison revealed that the present strain could be identified as *Rhizopus oryzae*, because: (1) The present strain can grow at 37° C.; (2) The sporangiospores are striate and measure 5-15×3-7 μm; (3) The sporangiophores measure 220-1200 μm in length; (4) The sporangia measure 60-150 μm in diameter.

Cloning of glucoamylase gene

The glucoamylase gene may be isolated in the form of cDNA prepared from the mRNA of Rhizopus or by cloning from the chromosomal DNA of Rhizopus using a synthetic origonucleotide corresponding to a part of amino acid sequence of Rhizopus glucoamylase.

Usually it is not easy to obtain the complete glucoamylase gene by the former method, while the gene obtained by the latter method usually contains intron sequences and thus cannot be expressed in host E. coli or yeast. In order to obtain a glucoamylase gene capable of expression in these hosts, an appropriate part of the cDNA from mRNA may be conjugated with the intron-free part of the DNA sequence of the chromosomal gene. If one or both DNA fractions lack suitable sites to be cleaved by restriction enzymes, a technique of in vitro mutagenesis may be employed to introduce suitable cleavage sites for conjugation purposes.

The glucoamylase gene used in the present invention involves not only the same nucleotide sequence coding for the bracketed amino acid sequence in FIG. 1a-c but also a nucleotide sequence corresponding to an amino acid sequence having an enzymatic activity comparable to that of the bracketed amino acids.

The Rhizopus-derived glucoamylase structural gene is a DNA fragment encoding the sequence of 26-604 amino acids from the N-terminal in FIG. 1a-c, or it corresponds to nucleotide sequence numbers 190-1926 designated in FIG. 1a-c. The region of 1-25 amino acids from the N-terminal is a signal peptide coding region involved in the extracellular secretion of glucoamylase from the host cell. When, as described below, glucoamylase was produced by a yeast using this signal peptide coding region, more than 90% of the glucoamylase produced was secreted in the culture medium. The secreted glucomaylase was purified by a routine method and the amino acid sequence at the N-terminus was examined; the amino acid sequence of the glucoamylase started at the 26th amino acid of the sequence given in FIG. 1a-c and this indicates that the region defined by 1-25 amino acids from the N-terminus will function as a signal peptide in the yeast as well.

A method that can be used with advantage for the purpose of isolating the glucoamylase gene shown above is described hereunder. The whole DNA is separated from a glucoamylase-producing fungus of the genus Rhizopus by a modified version of the method of Cryer et al. The microorganism is first sporulated and the spores produced are collected. The chromosomal DNA can be prepared from the fungal spores by first disrupting them with glass balls as described below in Example 1 (a-i). The mixture is then extracted by the method of Cryer et al. (Methods in cell Biology, 12:39-44 (1975)) and the extract is finally subjected to gel filtration. The resulting DNA fraction is digested with HindIII and cloned to the HindIII site of a known vector pBR322 to obtain a Rhizopus gene library in E. coli. The library may be recovered in the form of an ampicillin-resistant transformant.

A probe (DNA oligomer) described in Examples 1 and 2 for detecting glucoamylase gene is prepared and used in colony hybridization. Colonies that will hybridize with the probe are grown and the plasmid DNA is extracted.

The present invention is hereunder described in greater detail with reference to the following examples.

EXAMPLE 1

(a-i) DNA preparation and its cloning

The whole DNA was isolated from glucoamylase-producing Rhizopus oryzae. DNA isolation was performed by a modified version of the method of Cryer et al. that was described in Method in Cell Biology, vol. 12, pp. 39-44, 1975 and originally employed with yeasts. A thin potato slice was sterilized in an autoclave and the cells of Rhizopus oryzae were grown for sporulation. The spores produced were collected, suspended in a solution of 0.15M NaCl and 0.05M EDTA, and disrupted by treatment for 15 seconds in a Dyno mill using glass balls. Subsequent procedures were the same as those employed in the method of Cryer et al., except that in the last step, gel filtration using Biogel $A_{5m}$ (the tradename of Bio-Rad for a molecular sieve) was performed to isolate the whole DNA. This DNA fraction was digested with HindIII and cloned to the HindIII site of pBR322 to obtain a Rhizopus gene library in E. coli strain WA802. The strain was transformed by a routine method. The library was obtained as an ampicillin-resistant transformant.

(a-ii) Selection of transformant and characterization of the glucoamylase gene

Transformant selection was made by a method generally referred to as colony hybridization, using a nitrocellulose filter paper. The first step starts with the preparation of a probe for detecting the glucoamylase DNA. For this purpose, the purified Rhizopus glucoamylase was decomposed by a variety of proteases and the resulting peptides were separated and purified. These peptides were subjected to amino acid analysis and the primary structures were determined by routine methods. As a result, an amino acid sequence having the partial structure of Asp—Leu—Thr—Trp—Ser—His—Ala—Ser was obtained. It was also found that this glucoamylase had an N-terminal amino acid sequence of Ala—Ser—Ile—Pro and a C-terminal sequence of Ala—Ala. In order to prepare the desired probe, 32 different synthetic DNA oligomers each consisting of 14 bases (5'-ACNTGGTCNCAQGC-3') were produced by the triester solid-phase method from the amino acid sequence of Thr—Trp—Ser—His—Ala which was part of the sequence identified above and wherein N is an arbitrary base and Q is T or C from pyrimidine. These DNA oligomers were labelled with [$\gamma$-$^{32}$p]ATP and T4-polynucelotidyl kinase and used as probes for detecting the glucoamylase gene. Transformed E. coli colonies that hybridized with these probes by colony hybridization were grown and plasmid DNAs were extracted. The extract was treated with restriction enzymes and the resulting DNA fragments were analyzed by agarose-gel electrophoresis. As for the colonies that hybridized with the probes, the DNA fragment inserted in the plasmid had a size of 4.3 kb, as well as one cleavage site each of BamHI, KpnI, MluI and SacI, two sites for DraI and three sites for BglII, but had no cleavage sites for AccI, BalI, ClaI, EcoRI, HpaI, PstI, PvuII, ScaI or XhoI. The plasmid having this DNA fragment was named pRGA39.

(b-i) RNA preparation and cDNA cloning

The whole RNA was isolated from the aerial hyphae of Rhizopus oryzae. For this purpose, known procedures including the use of guanidium thiocyanate were followed. Polyadenylated RNA was recovered from the whole RNA as a mRNA fraction by way of chromatography on oligo-dT cellulose. Using this mRNA, a cDNA gene library was formed in E. coli WA802 by the method of Okayama and Berg described in Okayama, H. & Berg, P., Mol Cell Biol., 2, 161, 1982.

(b-ii) Transformant selection and characterization of glucoamylase cDNA

Selection of the transformant having the c-DNA of the glucoamylase was made by the aforementioned method of colony hybridization. A DraI fragment (2.0 kb) of the glucoamylase gene obtained in (a-ii) was used as a probe for detecting the glucoamylase cDNA. For this purpose, this fragment was labelled by the technique of nick translation using [$\alpha$-$^{32}$P]dCTP, DNA polymerase I and DNase I. The transformed colonies that would hybridize with this probe were allowed to grow and the plasmid DNA was extracted. The extract was treated with restriction enzymes and the resulting DNA fragments were analyzed by electrophoresis on agarose gel. The DNA fragment which had been inserted into the plasmid of the colonies that hybridized with the probe had a size of 1.7 kb. This plasmid was named pCGA239.

(c) Nucleotide DNA sequence analysis

Plasmids pRGA39 and pCGA239 were digested with restriction enzymes and DNA fragments were isolated on agarose gel. Their nucleotide sequences were determined by the dideoxy method using recombinant phage M13. Analysis of pRGA39 revealed that this gene contained four introns each having a length of several tens of bp (for the intron sites, see FIG. 2a–d. The plasmid pCGA239 was not a cDNA corresponding to the full length of glucoamylase but lacked about 50 amino acids. Restriction maps of pRGA39 and pCGA239 are compared in FIG. 4.

(d) Construction of glucoamylase gene to be expressed

Figure 5:
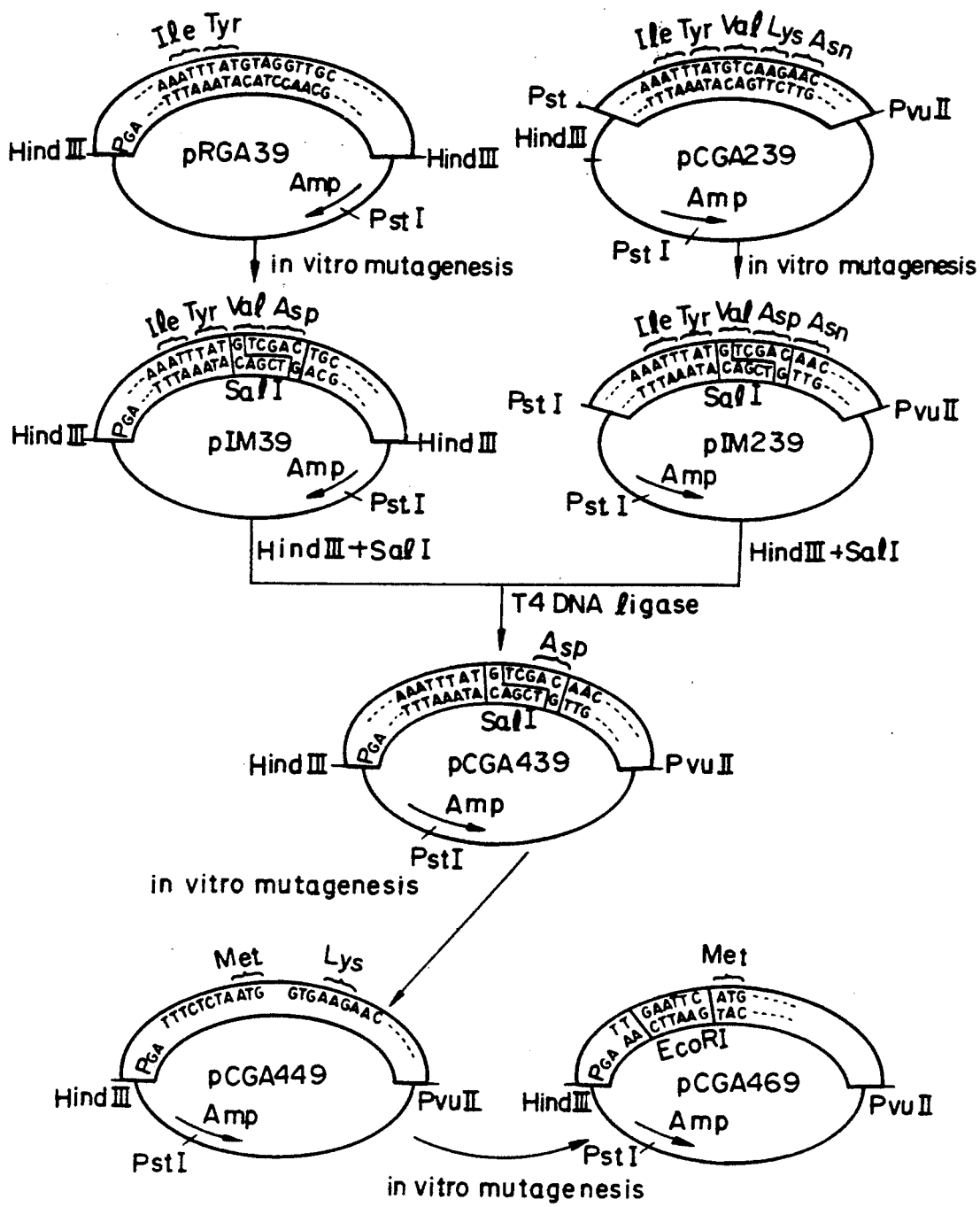

The cloned cDNA did not have the full length. A cDNA of the full length having in addition a glucoamylase promoter (derived from Rhizopus) was prepared by conjugating appropriate parts of pCGA239 and pRGA39. Since suitable restriction sites available for conjugation purposes were absent from the plasmids, the SalI site was introduced at the corresponding locations of pCGA239 and pRGA39 by the method of in vitro mutagenesis before performing the conjugation (see FIG. 5). For the method of in vitro mutagenesis, see Morinaga, Y. et al., BIO/THCHNOLOGY, 2, 636–639 (1984).

Because of the introduction of the SalI site, the 53rd amino acid codon from the N terminal of the treated plasmid PCGA439 was aspartic acid rather than lysine which was initially present. Therefore, the plasmid was again subjected to in vitro mutagenesis, whereby plasmid pCGA449 (deposited in the TRJ under accession number FERM BP-673) containing glucoamylase DNA of the full length having the inherent nucleotide sequence was obtained. This plasmid has been deposited with the Fermentation Research Institute, the Agency of Industrial Science and Technology, under designation of SAM0039 in accordance with the Budapest Treaty and has been assigned accession number FERM BP-673.

The full-length glucoamylase gene in pCGA449 is the combination of the sequence appearing before the arrow in FIG. 2(a) and the sequence appearing after the arrow in FIG. 3.

Figure 6A:
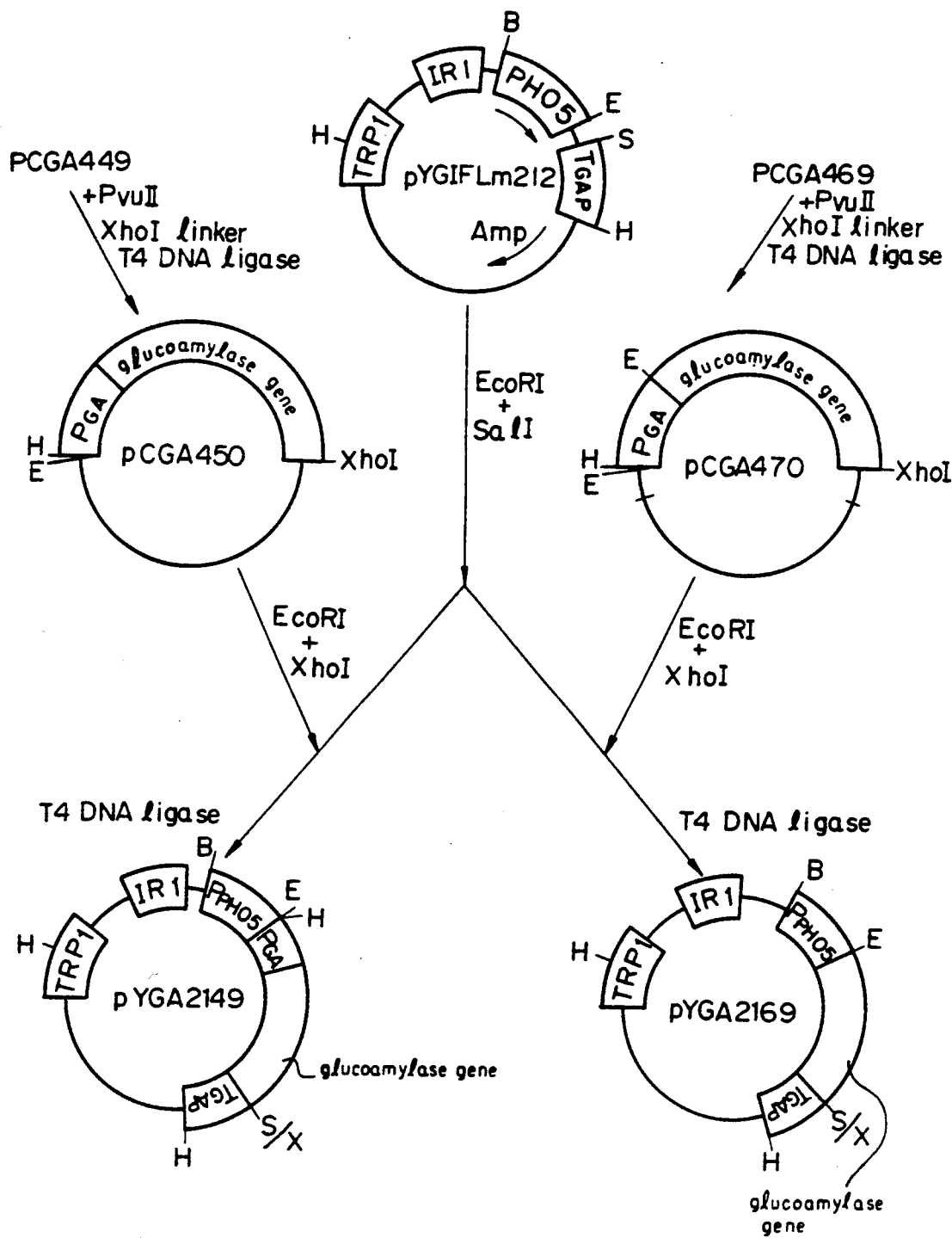
Figure 6B:
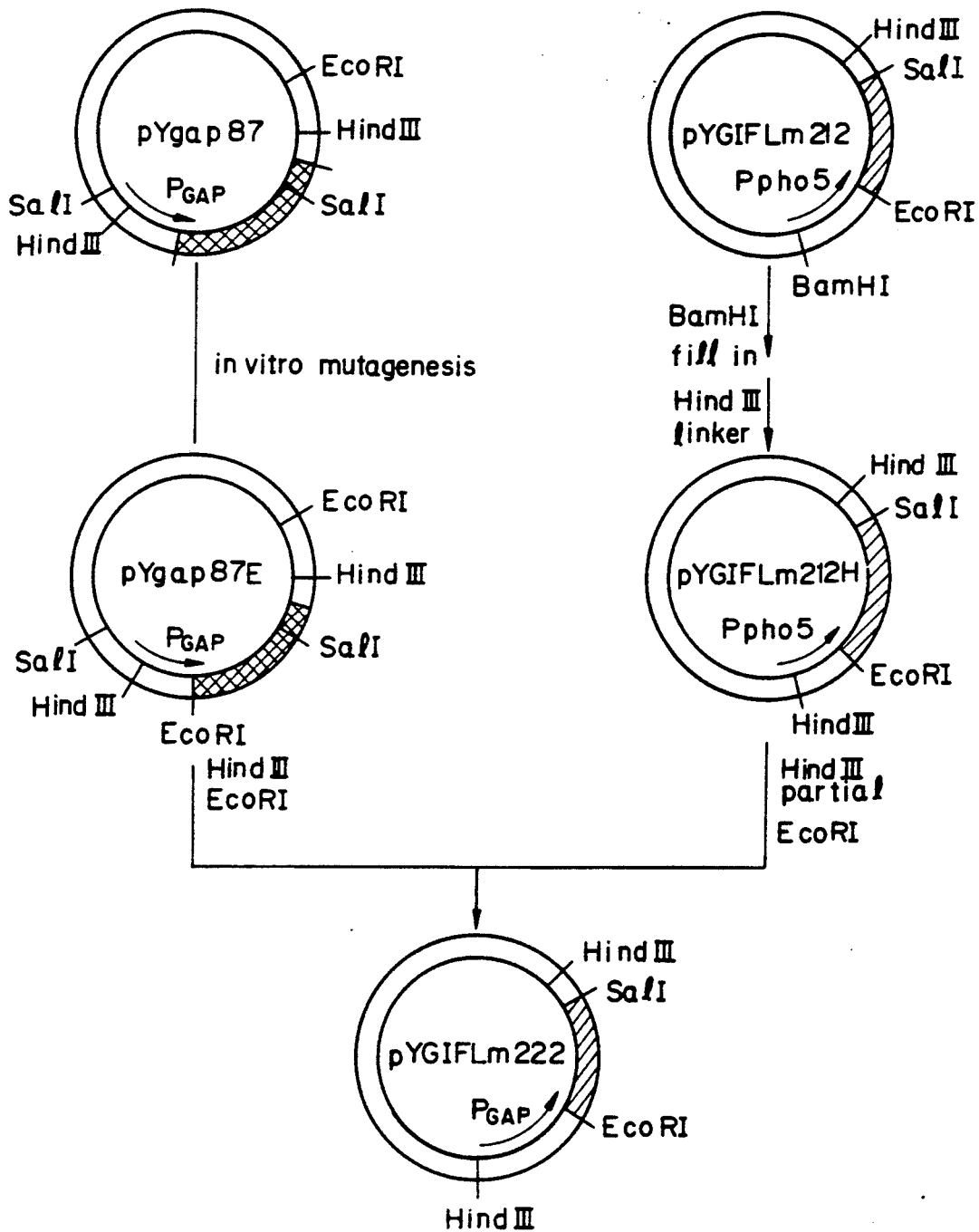
Figure 6C:
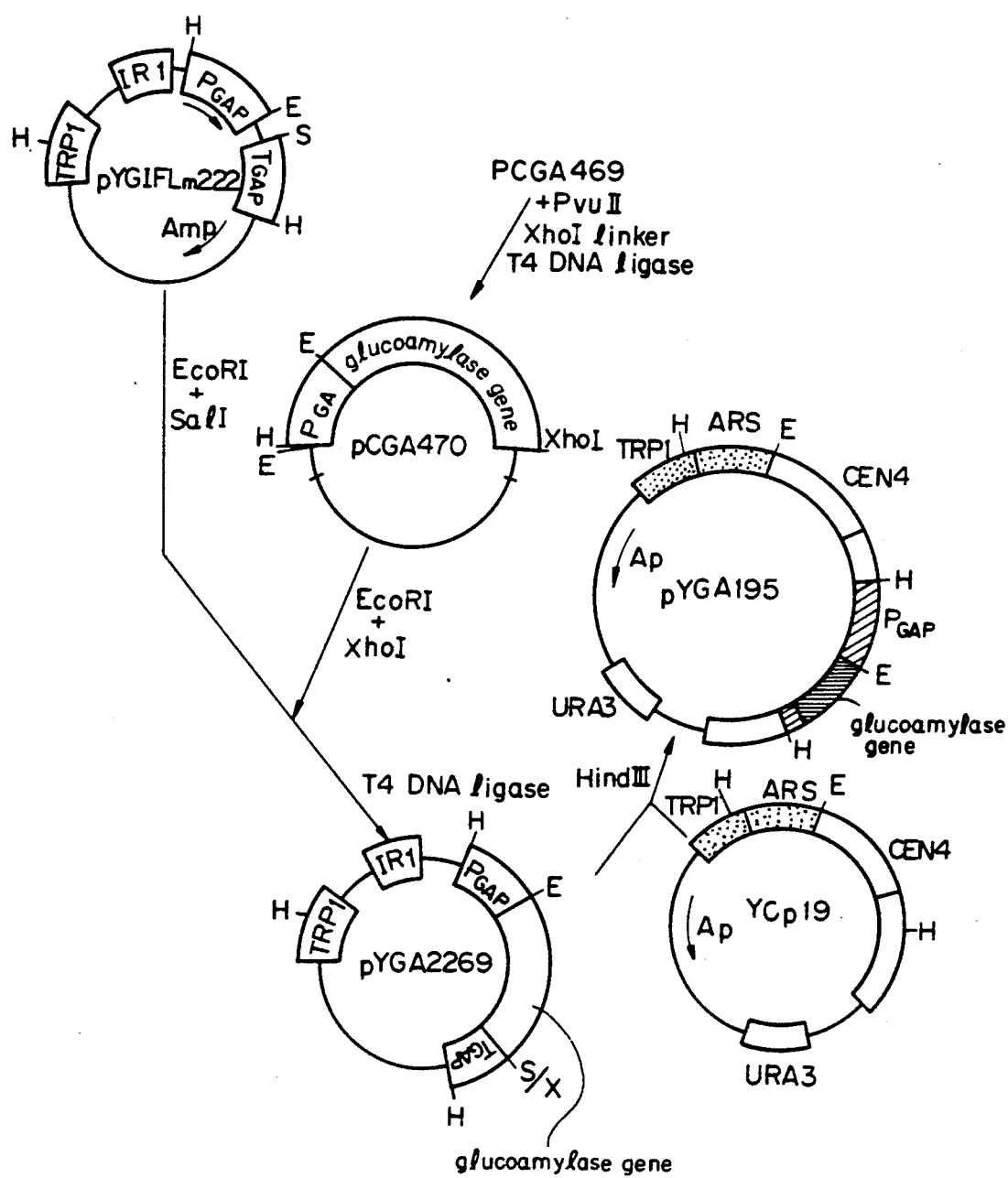
Figure 7:
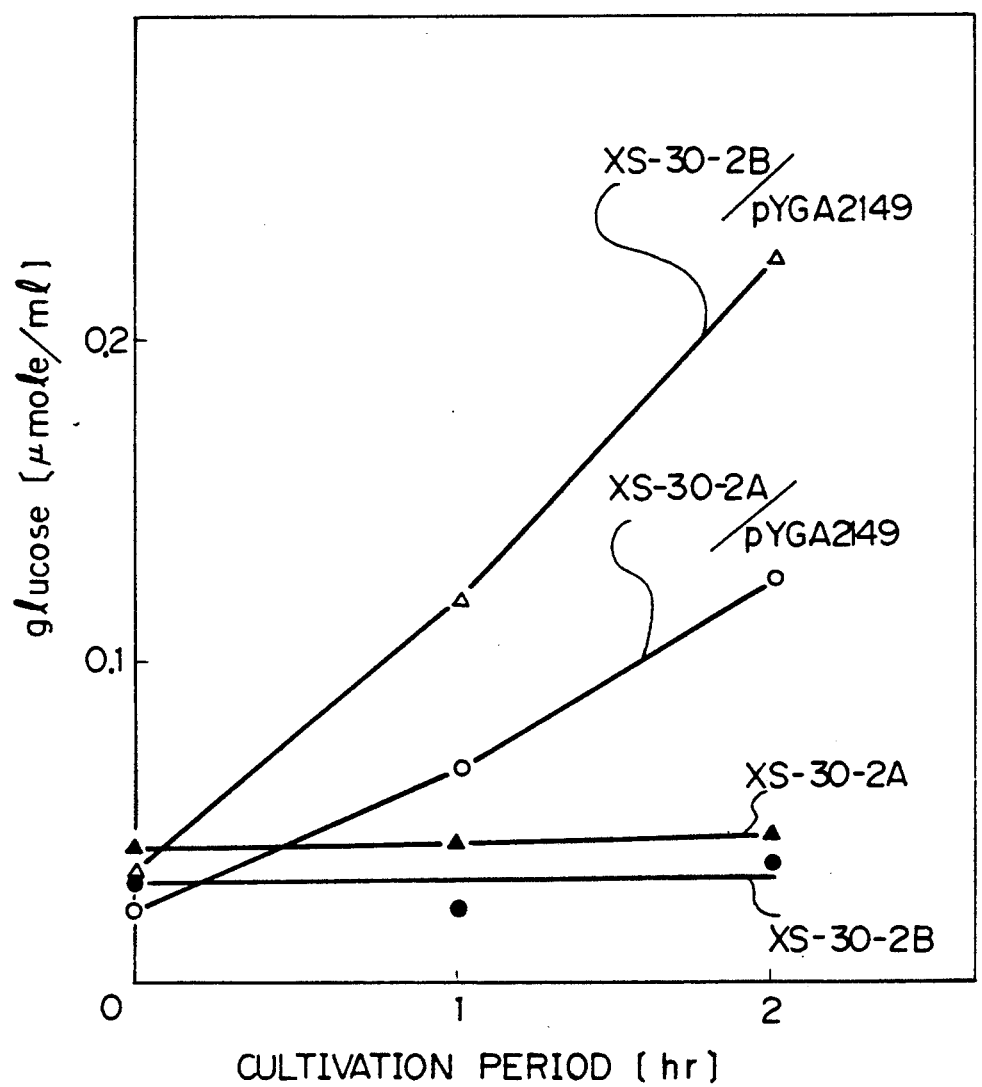
FIG. 7 is a graph showing the profile of glucoamylase production using transformed yeasts as performed in Example 1.

(e) Construction of expression vector in yeast (e-i) With a view to ensuring efficient expression of pCGA449 in a yeast, a fragment (ca. 8.3 kb) cut out with EcoRI-SalI from pYGIFLm212 (FRI accession number FERM BP-2216; converted from FERM P-7727) having the acid phosphatase promoter (Ppho5) disclosed in Japanese Patent Application No. 157037/1984 was used. The promoter Ppho5 is also contained in the plasmid deposited at FRI under accession number FERM BP-383. In order to incorporate pCGA449 at the EcoRI-SalI site, the PvuII site of pCGA449 was converted to XhoI site with XhoI linker, whereby plasmid pCGA450 was prepared (FIG. 6A). This plasmid was cleaved with XhoI and EcoRI and a 2.2 kb fragment was separated by agarose gel electrophoresis. This fragment was ligated to the previously obtained 8.3 kb EcoRI-SalI fragment with a T4-DNA ligase. The resulting plasmid containing Ppho5 as a promoter was named pYGA2149. This plasmid was grown in E. coli strain WA802 and then separated (see FIG. 6A). (e-ii) With a view to ensuring efficient expression of pCGA469 in a yeast, a fragment (ca. 8.9 kb) cut out with EcoRI-SalI from pYGIFLm222 having the glyceraldehyde-3-phosphate dehydrogenase promoter ($P_{GAP}$) disclosed in Japanese Patent Application No. 184291/1982 was used. In order to incorporate pCGA469 at the EcoRI-SalI site, the PvuII site of pCGA469 was converted to an XhoI site with a XhoI linker, whereby plasmid pCGA470 was prepared (FIG. 6C). This plasmid was cleaved with XhoI and EcoRI and a 2.2 kb fragment was separated by agarose gel electrophoresis. This fragment was ligated to the previously obtained 8.9 kb EcoRI-SalI fragment with a T4-DNA ligase. The resulting plasmid containing $P_{GAP}$ as a promoter was named pYGA2269. This plasmid was grown in E. coli strain WA802 and then separated (see FIG. 6C). The plasmid pYGIFLm222 used above was prepared (FIG. 6B) by replacing the expression promoter Ppho5 in pYGIFLm212 with a glyceraldehyde-3-phosphate dehydrogenase promoter ($P_{GAP}$ see Japanese Patent Application No. 184291/1982). Detailed procedures were as follows: the unique BamHI site in pYGIFLm212 was cleaved with BamHI, filled in with DNA polymerase I, and treated with a HindIII linker to convert the BamHI site to a HindIII site, whereby plasmid pYGIFLm212H was obtained. Using the technique of in vitro mutagenesis, an EcoRI site was introduced into pYgap87 (deposited in the FRI under accession number FERM BP-382) immediately upstream from ATG (the initiation codon for the replication of the structural gene of glyceraldehyde-3-phosphate dehydrogenase), whereby plasmid pYgap87E was prepared. The plasmid pYGIFLm212H was cleaved with EcoRI, further cleaved partially with HindIII and then subjected to agarose gel electrophoresis to isolate an 8.0 kb fragment. The plasmid pYgap87E was cut with EcoRI and HindIII and subjected to agarose gel electrophoresis to isolate a 1.1 kb fragment. This fragment was ligated with the foregoing 8.0 kb fragment of pYGIFLm212H and the resulting recombinant plasmid pYGIFLm222 was recovered from the transformed E. coli.

pYGA2169 was prepared from pYGIFLm212 using pCGA469 and repeating the same procedures as described above and the plasmid was separated (FIG. 6A).

pYGA2249 (not shown) was also prepared by the same procedures as described above and separated. (f) Expression of the glucoamylase gene in yeast The plasmid pYGA2149 was used to transform yeast [Saccharomyces cerevisiae strains XS-30-2A (MATα, leu2, his3, trpl, ura3) and XS-30-2B (MATα, leu2, his3, trpl, ura3)] and the transformed colonies were selected on the basis of the nutrient requirement for tryptophan as a marker. Transformation was performed by the method of Ito et al. (Ito, H. et al., J. Bacteriol., 153, 1983) using LiCl. A platinum loopful of the transformed colonies were inoculated in 5 ml of YPD medium (1% yeast extract, 2% polypeptone and 2% glucose) and sampling was made 48 hours later. Centrifugation (10,000 rpm×5 min) was conducted in an Eppendorf tube thus separating the sample into the supernatant and pellet. The activity of glucoamylase in the supernatant was measured by the following procedures: 200 ∞1 of the supernatant was added to 800 μl of a soluble starch solution (1.0% soluble starch in 20 mM acetate buffer solution, pH 5.0) and the mixture was left to stand at 37° C. The amount of released glucose was determined with a glucostat (Fujisawa Pharmaceutical Co., Ltd.). The activity data for the 2-hour reaction were as follows: 0.004 U/ml for pYGA2149 in XS-30-2A and 0.008 U/ml in XS-30-2B, indicating the sex-dependent difference by a factor of 2 (see FIG. 7). Activity of one unit (U) corresponds to 1 μmol of glucose released in 1 minute. No activity was observed in the supernatants obtained from yeast which did not contain pYGA2149.

The glucoamylase activity for the plasmid using $P_{GAP}$ as a promoter was 0.40 U/ml, which was 50–100 times the value for the case where such promoter was absent. The glucoamylase activity for the plasmid using the acid phosphatase gene promoter Ppho5 was dependent on the phosphate concentration of the medium. For example, no glucoamylase activity was observed after 48-hour cultivation in the ordinary YPD medium at 30° C., but an activity comparable to that for the use of $P_{GAP}$ appeared when the medium was replaced with YPD medium freed of phosphate by treatment with magnesium sulfate and ammonia water (Rubin, G. M., Eur. J. Biochem., 41, 197×202, 1974). The supernatant from the culture was subjected to SDS-polyacrylamide gel electrophoresis and no less than 50% of the total extracellular protein was glucoamylase protein.

Figure 8:
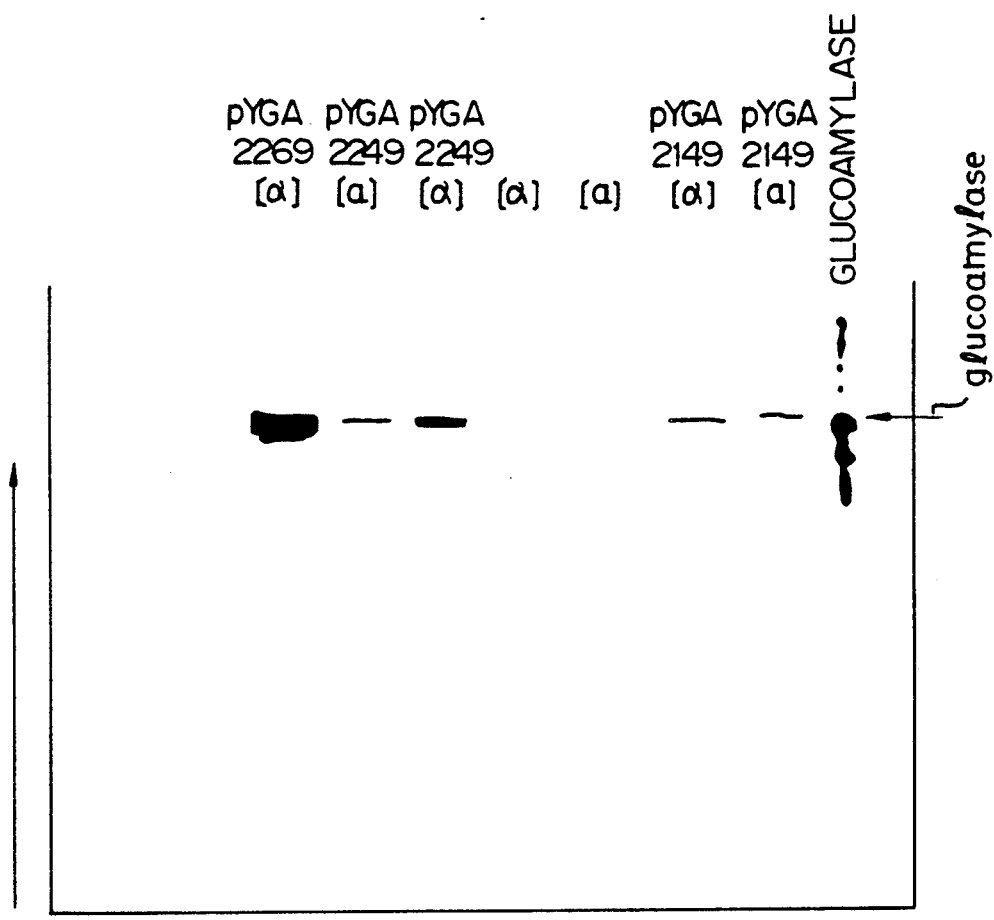
FIG. 8 is an electrophoretic diagram for glucoamylase samples produced by transformed yeasts in Example 1.

It was confirmed by the following immunological techniques that the activities listed above were due to the Rhizopus-derived glucoamylase. A rabbit antibody was prepared using a purified glucoamylase. This antibody was used in the analysis by a method commonly referred to as Western blotting, using a concentrate of 1.5 ml of the same supernatant from the 48-hour culture that was employed in the previous activity measurements. One third portion of the concentrate was subjected to 10% polyacrylamide electrophoresis and the protein in the gel was transferred and immobilized on a nitrocellulose filter paper electrophoretically. The glucoamylase on the nitrocellulose filter paper was then detected by the known technique in enzyme immunology using the reaction with peroxidase. A band that would react with the glucoamylase antibody emerged at a position substantially equal to the Rhizopus glucoamylase in terms of molecular weight. This fact did indicate the expression of the Rhizopus-derived glucoamylase in yeasts. The data showing this fact are give in FIG. 8.

(g) Growth of yeast using starch as a sole carbon source

Figure 9:
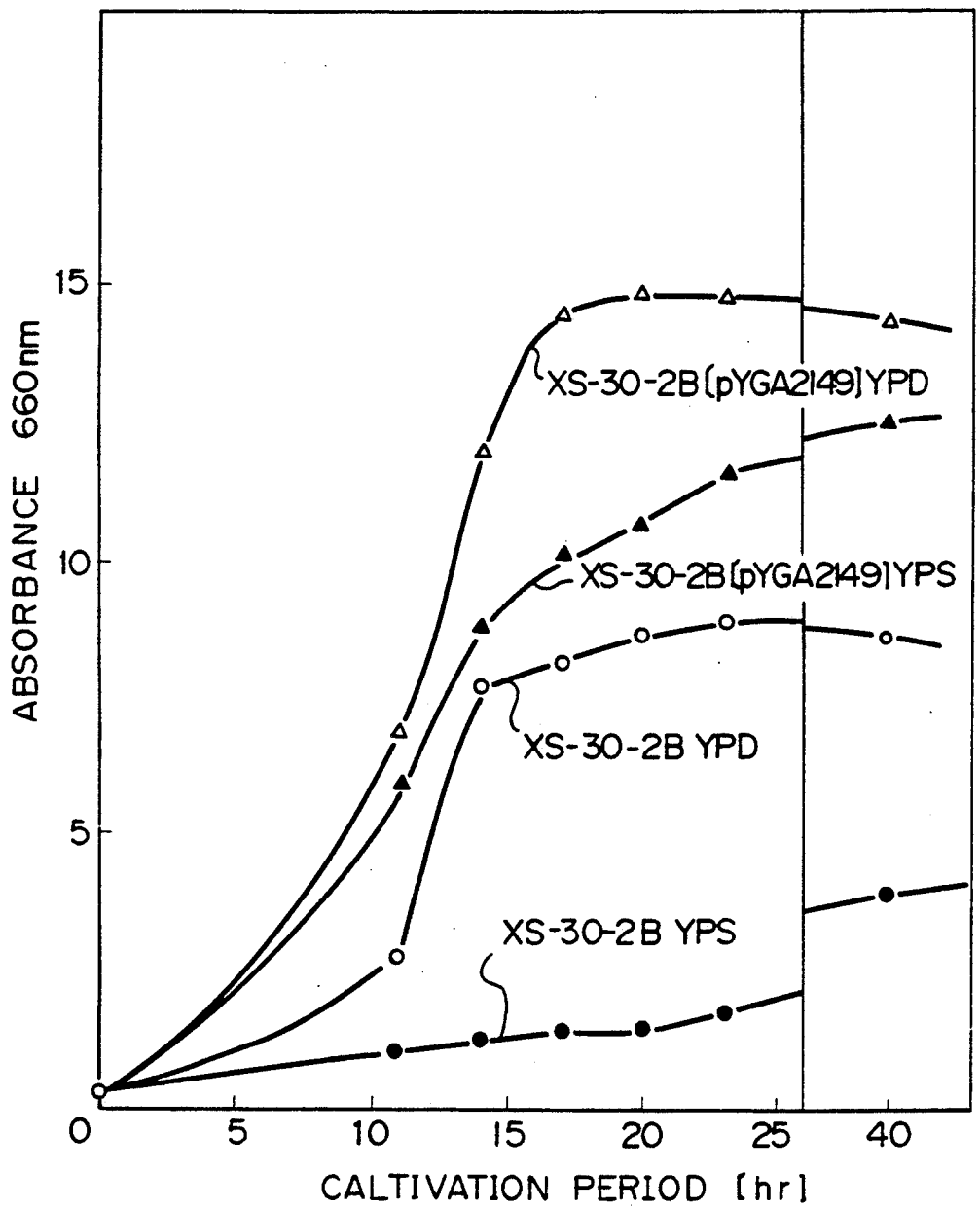
FIG. 9 is a graph showing growth curves for transformed yeasts that were cultured in Example 1 using starch as a sole carbon source.

The effect of pYGA2149 on the growth of yeast strain XS-30-2B was investigated using different carbon sources. First, XS-30-2B was shake-cultured in YPD medium for 24 hours at 30° C. and XS-30-2B (pYGA2149) was shake-cultured under the same conditions in a minimum nutrient medium (0.67% Difco Yeast nitrogen base and 2% glucose) containing 1% Casamino acids and uracil. A 100-ml portion each of YED medium or YPS medium (1% yeast extract, 2% polypeptone and 2% soluble starch) was added in a 500-ml Sakaguchi flask and sterilized in an autoclave. Each of the pre-culture suspensions (1 ml) was added to these mediums at 30° C. and the subsequent growth was evaluated in terms of absorbance at 660 nm. The strain XS-30-2B harboring no plasmid pYGA2149 was capable of little growth in the YPS medium, but the strain harboring pYGA2149 grew at equal rates on both YPS and YED mediums. This fact clearly shows that XS-30-2B (pYGA2149) produced glucoamylase and utilized the starch hydrolyzed by the enzyme (see FIG. 9).

(h) Alcohol production by transformed yeasts (h-i) Alcohol fermentation with soluble starch The medium used in this experiment was prepared by autoclaving (121° C., 15 minutes) 200 ml of YPS medium (1% yeast extract, 2% polypeptone, and 1, 2 or 5% soluble starch) in a 500-ml Erlenmeyer flask. The following yeast strains were employed.

(1) XS-30-2B (control having no glucoamylase gene);
(2) XS-30-2B (transformed by pYGA2149) having a Rhizopus promoter;
(3) XS-30-2B (transformed by pYGA2169) having the promoter Ppho5; and
(4) XS-30-2B (transformed by pYGA2269) having the promoter $P_{GAP}$.

Starting pre-culture was prepared by inoculating a platinum loopful of the yeast in a minimum nutrient medium (5 ml) containing 1% Casamino acids, uracil and adenine and shake-culturing at 28° C. for 20 hours. This starting preculture was inoculated in a YPD medium in an amount of two percent and subjected to stationary cultivation at 28° C. for 24 hours to obtain a final pre-culture. The final preculture was inoculated in YPS medium at five percent and subjected to stationary cultivation at 28° C. for the purpose of investigating ethanol production. The cultivation of yeast strain (3) on and after the final pre-culture was conducted in a low phosphate YPD or YPS medium respectively with a view to inducing Ppho5. The same experiment was conducted for three different starch concentrations (1, 2 and 5%). The results of ethanol production and yeast growth are shown in Tables 1 and 2.

TABLE 1

| No. | Yeast | Starch (%) | | 0 | 24 | 48 | 72 | 96 |
|---|---|---|---|---|---|---|---|---|
| 1 | XS-30-2B | 1 | GA (U/ml) | 0 | 0 | 0 | 0 | 0 |
|   |   |   | EtOH (v/v %) |   | 0.03 | 0.03 | 0.04 | 0.03 |
| 2 | [pYGA2149] | 2 | GA | 0 | 0 | 0 | 0 | 0 |
|   |   |   | EtOH |   | 0.03 | 0.02 | 0.03 | 0.05 |
| 3 |   | 2 | GA | 0 | 0 | 0 | 0 | 0 |
|   |   | 5 | EtOH |   | 0.03 | 0.03 | 0.04 | 0.03 |
| 4 | XS-30-2B | 1 | GA | 0.020 | 0.058 | 0.124 | 0.137 | 0.134 |
|   |   |   | EtOH |   | 0.12 | 0.19 | 0.44 | 0.29 |
| 5 | [pYGA2169] | 2 | GA | 0.020 | 0.069 | 0.339 | 0.399 | 0.429 |
|   |   |   | EtOH |   | 0.24 | 0.55 | 0.71 | 0.23 |
| 6 | 3 | 5 | GA | 0.020 | 0.031 | 0.488 | 0.763 | 0.833 |
|   |   |   | EtOH |   | 0.23 | 0.77 | (2.68) | 1.94 |
| 7 | XS-30-2B | 1 | GA | 0.030 | 0.041 | 0.091 | 0.089 | 0.116 |
|   |   |   | EtOH |   | 0.11 | 0.49 | 0.32 |   |
| 8 | [pYGA2269] | 2 | GA | 0.030 | 0.067 | 0.181 | 0.174 | 0.214 |
|   |   |   | EtOH |   | 0.34 | 1.00 | 0.68 |   |
| 9 | 4 | 5 | GA | 0.030 | 0.082 | 0.294 | 0.311 | 0.383 |
|   |   |   | EtOH |   | 0.33 | 1.92 | (2.12) |   |
| 10 | XS-30-2B | 1 | GA | 0 | 0 | 0 | 0 | 0 |
|   |   |   | EtOH |   | 0.03 | 0.03 | 0.02 |   |
| 11 | 1 | 2 | GA | 0 | 0 | 0 | 0 | 0 |
|   |   |   | EtOH |   | 0.03 | 0.04 | 0.04 |   |
| 12 |   | 5 | GA | 0 | 0 | 0 | 0 | 0 |
|   |   |   | EtOH |   | 0.03 | 0.03 | 0.03 |   |

GA: glucoamylase
EtOH: ethanol

TABLE 2

| | Utilization for 2% starch at 48 hour | | |
|---|---|---|---|
| Yeast | GA (U/ml) | EtOH (v/v %) | Yield (%) |
| XS-30-2B [pYGA2169] 3 | 0.34 | 0.55 | 40.4 |
| XS-30-2B [pYGA2269] 4 | 0.18 | 1.00 | 73.5 |
| XS-30-2B 1 | 0 | 0.04 | 0 |

(h-ii) Alcohol fermentation with low-temperature cooked starch

Ground corn (140 g) was added to 402 ml of water, and after adding 0.5 g of α-amylase preparation (Termamil) as a viscosity reducer and 160 ppm of potassium metabisulfite as a germicide, the mixture was held at 80°-82° C. for 5 minutes, and then rapidly cooled.

Figure 10:
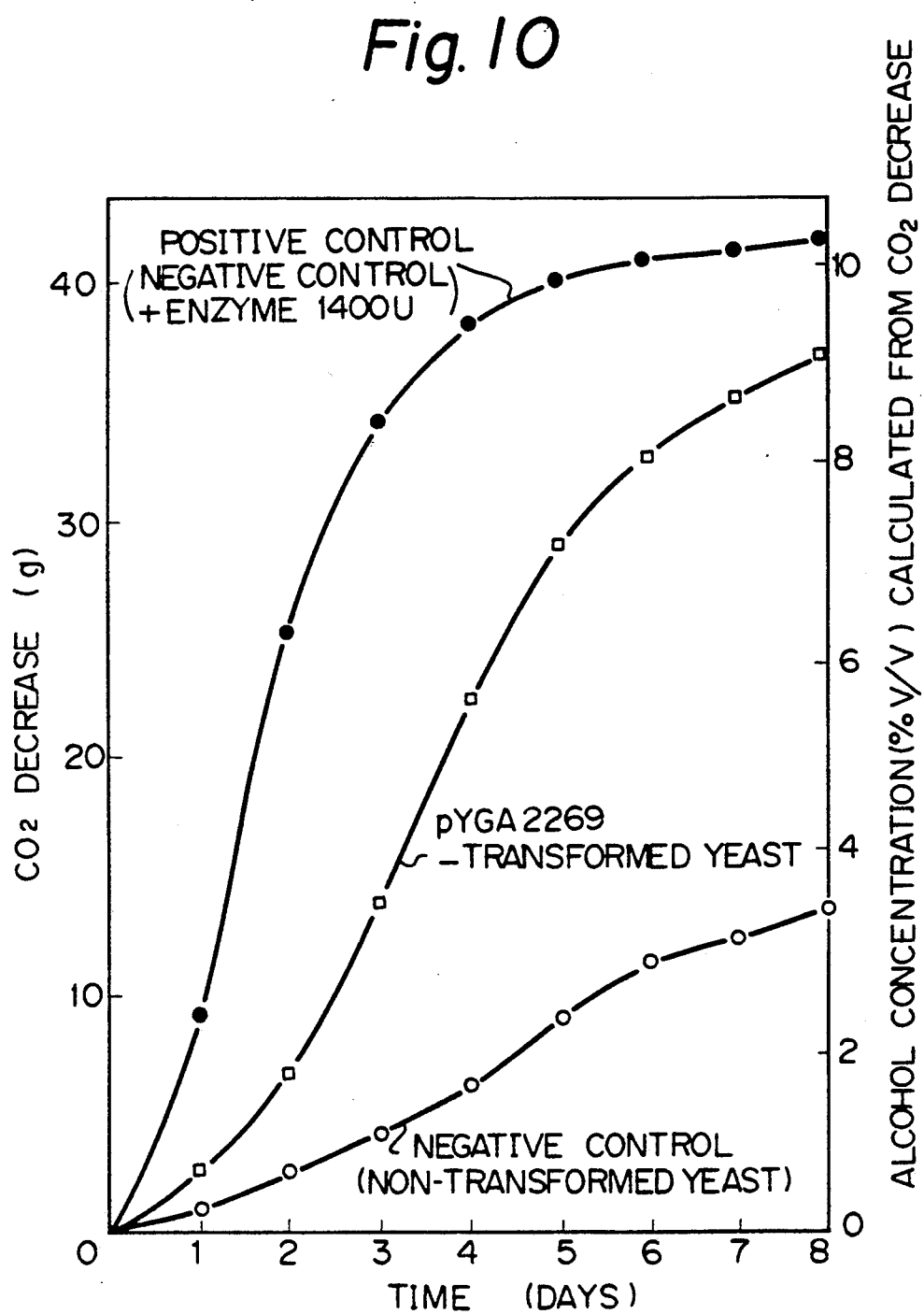
FIG. 10 is a graph showing the profile of alcohol production by one of the transformed yeasts prepared in Example 1.

Starting and final pre-cultures were prepared using the same strain as employed in (h-i) and the final pre-culture was added to the low-temperature cooked starch and the mixture was cultured at 28° C. under three different conditions, i.e., in the absence of any additional component, in the presence of Casamino acids, uracil and adenine, and in the presence of Casamino acids, uracil, adenine and 0.4% glucose. The progress of fermentation (as evaluated in terms of the decrease in $CO_2$) and alcohol production were investigated. A non-transformed yeast using the routine amount of Rhizopus glucoamylase was employed as a positive control. The results are shown in Tables 3 and 4 and in FIG. 10, from which one can see that the yeasts obtained in accordance with the present invention were capable of direct alcohol production from non-cooked or low-temperature cooked (LTC) starch without addition of a Rhizopus glucoamylase preparation.

cose, 0.001% uracil, 0.0054% adenine, 0.0026% leucine and 0.0038% histidine). The culture solution was inoculated at one percent in 400 ml of the minimum nutrient medium in an Erlenmeyer flask (1,000 ml) and shake-cultured at 30° C.

Sampling was conducted at approximate intervals of 3 hours, and the absorbance at 660 nm and the glucoamylase activity values at 24 and 48 hours were determined, by measuring the amount of free glucose that was released by reaction at 37° C. of a mixture of the supernatant of the culture (50 µl) and 950 µl of a soluble starch solution (0.5% soluble starch in 20 mM acetate buffer, pH 4.5). The amount of glucose was determined by a glucostat of Fujisawa Pharmaceutical Co., Ltd. One unit (U) of glucoamylase activity corresponds

TABLE 3

| | | $CO_2$ Reduction (g) | | | | | | | | |
|---|---|---|---|---|---|---|---|---|---|---|
| | | Casamino | | | | | Time (hrs) | | | |
| No. | Yeast | acids | Glucose | Enzyme* | 0 | 24 | 48 | 72 | 96 | 192 |
| 1 | XS-30-2B | | | | 0 | 0.33 | 3.05 | 6.62 | 11.4 | |
| 2 | [pYGA2149] | ○ | | | 0 | 0.51 | 3.85 | 6.00 | 7.15 | |
| 3 | ② | ○ | ○ | | 0 | 1.67 | 4.69 | 7.32 | 10.70 | |
| 4 | XS-30-2B | | | | 0 | 1.05 | 3.77 | 5.84 | 8.15 | |
| 5 | [pYGA2169] | ○ | | | 0 | 1.09 | 4.28 | 5.89 | 7.61 | |
| 6 | ③ | ○ | ○ | | 0 | 2.07 | 4.96 | 6.87 | 9.52 | |
| 7 | XS-30-2B | | | | 0 | 1.85 | 4.10 | 6.22 | 8.03 | |
| 8 | [pYGA2269] | ○ | | | 0 | 2.78 | 6.83 | 14.22 | 22.68 | 37.55 |
| 9 | ④ | ○ | ○ | | 0 | 3.89 | 8.18 | 13.75 | 19.17 | |
| 10 | XS-30-2B | | | | 0 | 0.65 | 2.38 | 2.97 | 4.04 | |
| 11 | (control) | ○ | | | 0 | 1.01 | 2.67 | 4.22 | 6.45 | 14.36 |
| 12 | ① | ○ | ○ | | 0 | 1.93 | 3.86 | 4.74 | 5.14 | |
| 13 | | ○ | | ○ | 0 | 9.25 | 25.43 | 34.14 | 38.38 | 42.27 |

Feed: 500 ml
*Rhizopus glucoamylase

TABLE 4

| | | Alcohol production (v/v %) | | | | | | | | |
|---|---|---|---|---|---|---|---|---|---|---|
| | | Casamino | | | | | Time (hrs) | | | |
| No. | Yeast | acids | Glucose | Enzyme* | 0 | 24 | 48 | 72 | 96 | 192 |
| 1 | XS-30-2B | | | | 0 | 0.0789 | 0.730 | 1.584 | 2.727 | |
| 2 | [pYGA2149] | ○ | | | 0 | 0.122 | 0.921 | 1.435 | 1.711 | |
| 3 | ② | ○ | ○ | | 0 | 0.400 | 1.122 | 1.751 | 2.560 | |
| 4 | XS-30-2B | | | | 0 | 0.251 | 0.902 | 1.397 | 1.950 | |
| 5 | [pYGA2169] | ○ | | | 0 | 0.261 | 1.024 | 1.409 | 1.821 | |
| 6 | ③ | ○ | ○ | | 0 | 0.495 | 1.187 | 1.344 | 2.278 | |
| 7 | XS-30-2B | | | | 0 | 0.443 | 0.981 | 1.488 | 1.921 | |
| 8 | [pYGA2269] | ○ | | | 0 | 0.665 | 1.634 | 3.402 | 5.426 | 9.0 |
| 9 | ④ | ○ | ○ | | 0 | 0.931 | 1.957 | 3.289 | 4.586 | |
| 10 | XS-30-2B | | | | 0 | 0.156 | 0.569 | 0.711 | 0.967 | |
| 11 | (control) | ○ | | | 0 | 0.242 | 0.639 | 1.009 | 1.543 | 3.4 |
| 12 | ① | ○ | ○ | | 0 | 0.462 | 0.923 | 1.134 | 1.230 | |
| 13 | | ○ | | ○ | | 2.213 | 6.084 | 8.167 | 9.182 | 10.1 |

Feed: 500 ml
*Rhizopus glucoamylase

EXAMPLE 2

(a) A 2.0 kb DNA fragment containing glucoamylase gene from pYGA2269 prepared in Example 1(e) was inserted into the HindIII site of a known vector YCp19, whereby pYGA195 was obtained (FIG. 6C). This plasmid, containing a centromere was present in yeast with a copy number of 1.

(b) Expression of glucoamylase gene in yeast

Figure 11:
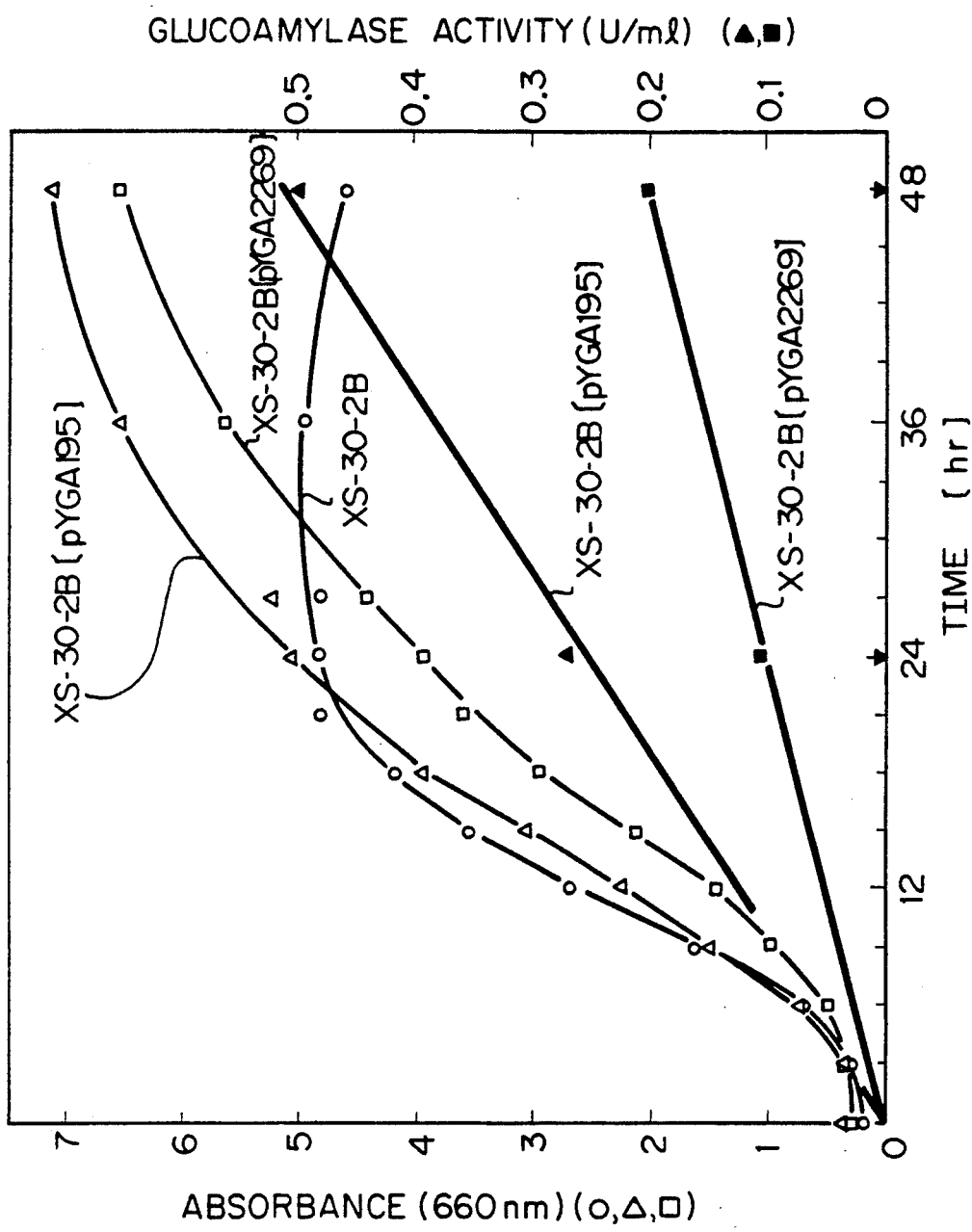
FIG. 11 is a graph showing the production of glucoamylase by the transformed yeasts obtained in Example 2.

The plasmids, pYGA2269 and pYGA195, were used to transform yeast strain XS-30-2B (MATα, Leu2, his3, trp1, ura3) and the transformed colonies were selected by the nutrient requirement for tryptophan as a marker. Transformation was conducted by the method of Ito et al (ibid) using LiCl. The selected transformed colonies were cultured overnight at 30° C. in 5 ml of a minimum nutrient medium (0.67% Yeast Nitrogen base, 2% gluto 1 µmole of glucose released in 1 minute. The yeasts transformed by pYGA2269 and pYGA195 produced glucoamylase activities in amounts of 0.2 U/ml and 0.5 U/ml, respectively, at 48 hours (see FIG. 11). This enzyme can be secreted in an adequate amount even from a plasmid with a copy number of 1 by expressing it in the presence of a strong promoter such as GAPDH promoter.

(c) Purification of the enzyme obtained by the recombinant DNA technology

S. cerevisiae XS-30-2B transformed by pYGA2269 was cultured for 3 days at 30° C. in a medium containing 0.67% Yeast Nitrogen base, 2% Casamino acids, 2% glucose, 0.001% uracil, 0.0054% adenine, 0.0026% leucine and 0.0038% histidine. The supernatant of the culture was concentrated about 20-folds by an Amicon concentrator, dialyzed against an acetate buffer (20 mM CH₃COONa, pH 4.6), and adsorbed on an SP-Sephadex C-50 column equilibrated with the same buffer. A linear gradient from 0 to 200 mmol was applied to the column, whereby the active fractions eluted were recovered, dialyzed against water, freeze-dried and stored for the following experiments.

(d) Properties of enzymes produced by the recombinant yeast was in good agreement with the Gluc 1 having the highest molecular weight of the three glucoamylase molecules produced by the Rhizopus; the N-terminal sequence and isoelectric point of the glucoamylase were also the same as those of the Rhizopus-produced glucoamylase. The apparent molecular weight of the glucoamylase as determined by SDS-polyacrylamide electrophoresis was slightly higher than that of Gluc 1. The molecular weight of the glucomaylase was decreased by digestion with endoglycosidase H capable of cutting a certain sugar chain attached to the asparagine residue. However, the Rhizopus-produced glucoamylase is not sensitive to the action of endoglycosidase H. The difference between the two glucoamylase molecules with respect to the molecular weight would be ascribable to the differences in the amount and mode of sugar chain attachment.

No difference was observed with respect to pH dependency, heat stability or other parameters such as Vmax and Km for soluble starch. The Rhizopus-produced glucoamylase had an r/s value (r: activity on raw starch, s: activity on gelatinized soluble starch) of 0.47 while the value for the recombinant yeast produced glucoamylase was 0.56. It is therefore concluded that as far as the ability to decompose raw starch is concerned, a better glucoamylase preparation can be produced from the recombinant yeast, rather than from the Rhizopus.

(e) Adsorption site on starch

The Rhizopus-produced glucoamylase contains three molecules having different molecular weights, Gluc 1, 2 and 3, the last two of which would be the product of limited proteolysis of the N-terminal amino acid sequence of Gluc 1.

The behavior of these three molecules in adsorption to starch was investigated. A sample of enzyme solution was mixed with an equal volume of raw starch and, after leaving the mixture to stand in iced water for 30 minutes, it was subjected to centrifugation. The supernatant was recovered as a fraction of the enzyme which was not adsorbed on the starch while the precipitate was recovered as a fraction which was adsorbed on starch. Both fractions were analyzed by SDS-PAGE; Gluc 1 and the recombinant yeast produced glucoamylase were found in the precipitate whereas Gluc 2 and 3 were found in the supernatant. The mixture of Gluc 2 and 3 had an r/s value of 0.23, indicating that the Rhizopus glucomaylase lost its ability to be adsorbed onto raw starch by becoming deficient of the N-terminal sequence. It is therefore concluded that the N-terminal portion has a site which is adsorbed on raw starch. The Rhizopus glucoamylase was capable of hydrolysing gelatinized soluble starch as effectively as the glucoamylase of the full length even if it lost the N-terminal portion. When a mixture of glucoamylase solution with gelatinized soluble starch was subjected to column chromatography on Ultrogel AcA 44, both Gluc 1 and the recombinant yeast produced glucomaylase were eluted in the void volumes in the column together with the starch, but neither Gluc 2 nor 3 was adsorbed on the starch and they were eluted in the corresponding elution volumes. This provided a basis for the conclusion that Gluc 1 and the recombinant yeast produced glucoamylase are capable of adsorption not only on raw starch but also on gelatinized starch.

What is claimed is:

1. A process for producing ethanol from a starchy material, wherein the starchy material is simultaneously subjected to saccharification and subsequent fermentation by use of a yeast host which has been transformed by an expressible recombinant vector comprising a glucoamylaser gene encoding a polypeptide comprising the amino acid sequence (III):

(Sequence III)

10
MET GLN LEU PHE ASN LEU PRO LEU LYS VAL SER

20
PHE PHE LEU VAL LEU SER TYR PHE SER LEU LEU

30
VAL SER ALA Ala Ser Ile Pro Ser Ser Ala Ser Val Gln Leu 40    50
Asp Ser Tyr Asn Tyr Asp Gly Ser Thr Phe Ser Gly Lys Ile Tyr

60
Val Lys Asn Ile Ala Tyr Ser Lys Lys Val Thr Val Ile Tyr Ala 70    80
Asn Gly Ser Asp Asn Trp Asn Asn Asn Gly Asn Thr Ile Ala Ala

90
Ser Tyr Ser Ala Pro Ile Ser Gly Ser Asn Tyr Glu Tyr Trp Thr 100    110
Phe Ser Ala Ser Ile Asn Gly Ile Lys Glu Phe Tyr Ile Lys Tyr

120
Glu Val Ser Gly Lys Thr Tyr Tyr Asp Asn Asn Asn Ser Ala Asn 130    140
Tyr Gln Val Ser Thr Ser Lys Pro Thr Thr Thr Thr Ala Thr Ala

150
Thr Thr Thr Thr Ala Pro Ser Thr Ser Thr Thr Pro Pro Ser 160    170
Ser Ser Glu Pro Ala Thr Phe Pro Thr Gly Asn Ser Thr Ile Ser

180
Ser Trp Ile Lys Lys Gln Glu Gly Ile Ser Arg Phe Ala Met Leu 190    200
Arg Asn Ile Asn Pro Pro Gly Ser Ala Thr Gly Phe Ile Ala Ala

210
Ser Leu Ser Thr Ala Gly Pro Asp Tyr Tyr Tyr Ala Trp Thr Arg 220    230
Asp Ala Ala Leu Thr Ser Asn Val Ile Val Tyr Glu Tyr Asn Thr

240
Thr Leu Ser Gly Asn Lys Thr Ile Leu Asn Val Leu Lys Asp Tyr 250    260
Val Thr Phe Ser Val Lys Thr Gln Ser Thr Ser Thr Val Cys Asn

270
Cys Leu Gly Glu Pro Lys Phe Asn Pro Asp Gly Ser Gly Tyr

280
Thr Gly Ala Trp Gly Arg Pro Gln Asn Asp Gly Pro Ala Glu 290    300
Arg Ala Thr Thr Phe Ile Leu Phe Ala Asp Ser Tyr Leu Thr Gln

(Sequence III)

310
Thr Lys Asp Ala Ser Tyr Val Thr Gly Thr Leu Lys Pro Ala Ile 320              330
Phe Lys Asp Leu Asp Tyr Val Val Asn Val Trp Ser Asn Gly

340
Cys Phe Asp Leu Trp Glu Glu Val Asn Gly Val His Phe Tyr 350              360
Thr Leu Met Val Met Arg Lys Gly Leu Leu Leu Gly Ala Asp

370
Phe Ala Lys Arg Asn Gly Asp Ser Thr Arg Ala Ser Thr Tyr Ser 380              390
Ser Thr Ala Ser Thr Ile Ala Asn Lys Ile Ser Ser Phe Trp Val

400
Ser Ser Asn Asn Trp Ile Gln Val Ser Gln Ser Val Thr Gly Gly 410              420
Val Ser Lys Lys Gly Leu Asp Val Ser Thr Leu Leu Ala Ala Asn

430
Leu Gly Ser Val Asp Asp Gly Phe Phe Thr Pro Gly Ser Glu Lys 440              450
Ile Leu Ala Thr Ala Val Ala Val Glu Asp Ser Phe Ala Ser Leu

460
Tyr Pro Ile Asn Lys Asn Leu Pro Ser Tyr Leu Gly Asn Ser Ile 470              480
Gly Arg Tyr Pro Glu Asp Thr Tyr Asn Gly Asn Gly Asn Ser

490
Gln Gly Asn Ser Trp Phe Leu Ala Val Thr Gly Tyr Ala Glu

500
Leu Tyr Tyr Arg Ala Ile Lys Glu Trp Ile Gly Asn Gly Gly Val 510              520
Thr Val Ser Ser Ile Ser Leu Pro Phe Phe Lys Lys Phe Asp Ser

530
Ser Ala Thr Ser Gly Lys Lys Tyr Thr Val Gly Thr Ser Asp Phe 540              550
Asn Asn Leu Ala Gln Asn Ile Ala Leu Ala Ala Asp Arg Phe Leu

560
Ser Thr Val Gln Leu His Ala His Asn Asn Gly Ser Leu Ala Glu 570              580
Glu Phe Asp Arg Thr Thr Gly Leu Ser Thr Gly Ala Arg Asp

590
Leu Thr Trp Ser His Ala Ser Leu Ile Thr Ala Ser Tyr Ala Lys

600
Ala Gly Ala Pro Ala Ala.

2. A process according to claim 1, wherein the glucoamylase gene is derived from fungus of *Rhizopus oryzae*.

3. A process according to claim 1, wherein the vector is selected from the group consisting of plasmid pCGA449, pCGA469, pYGA22149, PYGA2169 and pYGA195.

4. A process according to claim 1, wherein the host is Saccharomyces cerevisiae.

5. A process according to claim 1, wherein the glucoamylaser gene comprises nucleotide sequence (IV):

(Sequence IV)

```
                                                                        180
ATG CAA CTG TTC AAT TTG CCA TTG AAA GTT TCA TTC TTT CTC GTC CTC TCT TAC TTT TCT TTG CTC GTT
                                                                        240
TCT GCT GCA AGC ATT CCT AGT AGT GCT TCT GTC CAG CTT GAT TCA TAC AAT TAC GAT GGC TCT ACT TTT
                                                300
TCA GGA AAA ATT TAT GTC AAG AAC ATT GCT TAC TCC AAG AAG GTT ACT GTA ATT TAG GCC GAT GGC
                                        360
TCT GAC AAC TGG AAT AAT AAT GGA AAC ACC ATT GCT GCT TCT TAC TCT GCT CCT ATT TCT GGA TCA
                                420
AAT TAC GAA TAC TGG ACA TTC TCT GCC TCC ATT AAT GGT ATC AAG GAG TTC TAC ATT AAG TAT GAG GTC
                        480
AGT GGA AAA ACA TAC TAT GAT AAC AAC AAT TCT GCC AAT TAC CAA GTA TCT ACA TCC AAG CCT ACT ACT
                540
ACT ACT GCT ACT GCT ACT ACT ACT ACC GCT CCT TCC ACT TCA ACC ACG ACT CCC CCC TCA AGC TCT GAG
        600
CCA GCT ACT TTC CCA ACT GGT AAC TCT ACA ATC TCC TCA TGG ATT AAG AAG CAA GAA GGT ATC AGC
660                                                                720
CGC TTT GCT ATG CTT CGA AAC ATC AAT CCT CCT GGA AGC GCT ACC GGT TTC ATT GCT GCC TCA CTC TCT
                                                        780
ACC GCT GGT CCC GAT TAC TAC TAT GCT TGG ACT CGT GAT GCT GCA TTA ACC TCC AAT GTA ATT GTT TAC
                                                840
GAA TAC AAC ACT ACT TTG TCC GGT AAT AAG ACT ATC CTC AAC GTC CTC AAG GAC TAT GTT ACA TTC TCA
                                        900
GTC AAG ACC CAA TCA ACT TCT ACC GTC TGT AAC TGC CTT GGT GAG CCT AAG TTC AAT CCT GAT GGT TCT
                                960
GGC TAT ACT GGT GCT TGG GGA AGA CCT CAA AAT GAT GGA CCT GCT GAA CGT GCT ACT ACC TTC ATT
                        1020
TTG TTT GCT GAC AGT TAT CTT ACT GAA ACA AAG GAT GCT TCC TAT GTC ACT GGT ACA CTC AAG CCT
                1080
GTC ATC TTC AAG GAC TTG GAC TAT GTC GTC AAT GTC TGG TCT AAT GGC TGT TTC GAT TTA TGG GAA GAA
1140                                                            1200
GTC AAC GGT GTT CAC TTC TAT ACT TTA ATG GTT ATG CGT AAG GGT TTG CTT CTT GGT GCA GAT TTC GCT
                                        1260
AAA CGT AAC GGT GAC TCT ACT CGT GCA TCT ACC TAT AGC AGC ACT GCA TCC ACT ATT GCA AAC AAG ATC
                                1320
TCT AGC TTC TGG GTT TCT TCT AAT AAC TGG ATT CAA GTC AGT CAA AGC GTT ACT GGT GGT GTC AGT
                        1380
AAA AAG GGT TTG GAT GTC TCC ACA TTG TTG GCT GCT AAC CTT GGT AGT GTT GAT GAT GGA TTC TTC ACT
                1440
CCT GGC TCT GAA AAG ATC CTT GCC ACT GCT GTT GCT GTT GAA GAC TCC TTC GCT TCC TTG TAT CCT ATC
        1500
AAC AAA AAC CTT CCA TCT TAC CTT GGT AAC TCT ATT GGT AGA TAT CCT GAA GAC ACT TAC AAT GGT AAC
```

-continued
(Sequence IV)

```
                1560
GGA AAC TCT CAA GGA AAC TCT TGG TTC TTG GCT GTA ACT GGT TAC GCT GAG CTC TAT TAC CGT GCC
          1620
ATC AAG GAA TGG ATC GGC AAC GGT GGT GTC ACT GTC AGC AGC ATA AGT TTA CCC TTC TTC AGG AGG
1680                                                                          1740
TTT GAT TCA TCT GCT ACA TCT GGA AAG AAG TAC ACT GTT GGT ACC TCC GAC TTT AAC AAC CTT GCT CAA
                                                   1800
AAT ATT GCA CTC GCT GCT GAC CGT TTC TTG TCC ACT GTC CAG CTC CAT GCT CAC AAC AAT GGA TCT CTT

GCT GAA GAG TTT GAC CGC ACC ACT GGT TTA TCC ACC GGT GCT AGA GAC TTG ACC TGG TCT CAC GCT

TCT TTA ATC ACC GCT TCT TAC GCT AAG GCT GGT GCA CCT GCC GCT.
```

6. A process according to claim 1, wherein the glucoamylaser gene is linked with a DNA sequence capable of effecting expression of the gene encoding said polypeptide.

* * * * *